(12) United States Patent
Fay et al.

(10) Patent No.: US 7,855,274 B2
(45) Date of Patent: Dec. 21, 2010

(54) RECOMBINANT FACTOR VIII HAVING INCREASED SPECIFIC ACTIVITY

(75) Inventors: Philip J. Fay, Pittsford, NY (US); Hironao Wakabayashi, Rochester, NY (US)

(73) Assignee: University of Rochester, Rochester, NY (US)

( * ) Notice: Subject to any disclaimer, the term of this patent is extended or adjusted under 35 U.S.C. 154(b) by 483 days.

(21) Appl. No.: 10/581,471

(22) PCT Filed: Dec. 2, 2004

(86) PCT No.: PCT/US2004/040234
§ 371 (c)(1),
(2), (4) Date: Aug. 31, 2006

(87) PCT Pub. No.: WO2005/055930
PCT Pub. Date: Jun. 23, 2005

(65) Prior Publication Data
US 2007/0265199 A1    Nov. 15, 2007

Related U.S. Application Data

(60) Provisional application No. 60/526,664, filed on Dec. 3, 2003.

(51) Int. Cl.
*A61K 38/00* (2006.01)
*A61K 38/37* (2006.01)
(52) U.S. Cl. .................... 530/383; 514/12
(58) Field of Classification Search .............. None
See application file for complete search history.

(56) References Cited

U.S. PATENT DOCUMENTS

| | | | |
|---|---|---|---|
| 5,422,260 A * | 6/1995 | Kaufman et al. ........... 514/21 |
| 5,576,291 A | 11/1996 | Curtis et al. |
| 5,859,204 A * | 1/1999 | Lollar .................... 530/383 |
| 5,880,327 A | 3/1999 | Lubon et al. |
| 5,998,589 A | 12/1999 | Buettner et al. |
| 6,271,025 B1 | 8/2001 | Négrier et al. |
| 6,376,463 B1 | 4/2002 | Lollar |
| 6,458,563 B1 | 10/2002 | Lollar |
| 6,593,291 B1 | 7/2003 | Green et al. |
| 6,599,724 B1 | 7/2003 | Mikaelsson et al. |
| 6,759,216 B1 | 7/2004 | Lollar |
| 6,770,744 B2 | 8/2004 | Lollar |
| 6,780,614 B2 | 8/2004 | Négrier et al. |
| 6,800,461 B2 | 10/2004 | Négrier et al. |
| 2003/0125232 A1 | 7/2003 | Griffin et al. |
| 2003/0166536 A1 | 9/2003 | Lollar et al. |
| 2004/0092442 A1 | 5/2004 | Kaufman et al. |
| 2004/0147436 A1 | 7/2004 | Kim et al. |
| 2004/0197875 A1 | 10/2004 | Hauser et al. |
| 2005/0100990 A1* | 5/2005 | Saenko et al. ........... 435/69.6 |

OTHER PUBLICATIONS

Wakabayashi et al., "Ca2+ Binding to Both the Heavy and Light Chains of Factor VIII Is Required for Cofactor Activity," Biochem. 41:8485-8492 (2002).
Wakabayashi et al., "Residues 110-126 in the Factor VIII Heavy Chain Contain a Ca2+ Binding Site Required for Cofactor Activity," Blood 102(11):542a (2003).
Amano et al., "Mutation at either ARg336 or Arg562 in Factor VIII is Insufficient for Complete Resistance to Activated Protein C (APC)-Mediated Inactivation: Implications for the APC Resistance Test," Thromb Haemost 79:557-563 (1998).
Swaroop et al., "Mutagenesis of Potential Immunoglobulin-Binding Protein-Binding Site Enhances Secretion of Coagulation Factor VIII," J Biol Chem 272(39):24121-24124 (1997).
Wakabayahi et al., "Factor VIII: E113A Represents a High Specific Activity Factor VIII Arising From a Single Point Mutation within the Ca2+ Binding Site," Blood 104(11):479a (2004).
Wakabayashi et al., "Residues 110-126 in the A1 Domain of Factor VIII Contain a Ca2+ Binding Site Required for Cofactor Activity," J Biol Chem 279(13:12677-12684 (2004).
Sarafanov et al., "Cell Surface Heparan Sulfate Proteoglycans Participate in Factor VIII Catabolism Mediated by Low Density Lipoprotein Receptor-Related Protein," J Biol Chem 276(15):11970-11979 (2001).
Lenting et al., "The Sequence of Glu1811-Lys1818 of Human Blood Coagulation Factor VIII Comprises a Binding Site for Activated Factor 1X," J Biol Chem 271(4):1935-1940 (1996).
Gale et al., "An Engineered Interdomain Disulfide Bond Stabilizes Human Blood Coagulation Factor VIIIa," J Thrombosis and Haemostasis 1(9):1966-1971 (2003) (abstract only).
Pipe et al., "Characterization of a Genetically Engineered Inactivation-Resistant Coagulation Factor VIIIa," Proc Natl Acad Sci USA 94:11851-11856 (1997).
Lenting et al., "The Life Cycle of Coagulation Factor VIII in View of Its Structure and Function," Blood 92(11):3983-3996 (1998).
Hernández (editor), "Factor VIII/von Willebrand Factor Complex in Hemophilia A Treatment Recent Findings, Emerging Major Role," Journal of Hematology 88(9):1-27 (2003).

* cited by examiner

*Primary Examiner*—David J Steadman
*Assistant Examiner*—Marsha M Tsay
(74) *Attorney, Agent, or Firm*—Nixon Peabody LLP

(57) ABSTRACT

The present invention relates to recombinant factor VIII having a specific activity that is higher than that of the corresponding wild-type factor VIII. The present invention also relates to methods of making and using the recombinant factor VIII. The present invention also relates to an isolated nucleic acid molecule that encodes the recombinant factor VIII, as well as DNA expression systems and host cells containing the isolated nucleic acid molecule.

16 Claims, 15 Drawing Sheets

Factor VIII  $^{110}$EGAEYDDQTSQREKEDD
Factor V    $^{96}$EGASYLDHTFPAEKMDD

Figure 5 human Factor VIII    $^{110}$EGAEYDDQTSQREKEDD
porcine Factor VIII  $^{110}$EGAEYEDHTSQREKEDD
murine Factor VIII   $^{110}$EGDEYEDQTSQMEKEDD
canine Factor VIII   $^{110}$EGAEYEDQTSQKEKEDD

Figure 6

SEQUENCE LISTING

<160> NUMBER OF SEQ ID NOS: 7

<210> SEQ ID NO 1
<211> LENGTH: 6999
<212> TYPE: DNA
<213> ORGANISM: Human

<400> SEQUENCE: 1

```
gccaccagaa gatactacct gggtgcagtg gaactgtcat gggactatat gcaaagtgat      60
ctcggtgagc tgcctgtgga cgcaagattt cctcctagag tgccaaaatc tttttccattc    120 aacacctcag tcgtgtacaa aaagactctg tttgtagaat tcacggatca ccttttcaac    180
atcgctaagc caaggccacc ctggatgggt ctgctaggtc ctaccatcca ggctgaggtt    240
tatgatacag tggtcattac acttaagaac atggcttccc atcctgtcag tcttcatgct    300
```

```
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttgct    600 gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg acagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaagtccg atttatggca tacacagatg aaacctttaa gactcgtgaa   1320
gctattcagc atgaatcagg aatcttggga cctttacttt atggggaagt tggagacaca   1380
ctgttgatta tatttaagaa tcaagcaagc agaccatata acatctaccc tcacggaatc   1440
actgatgtcc gtccttttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctgtagat   1680
caaagaggaa accagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860 gttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg ggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat gaaccaaga   2220 agcttctccc agaattcaag acaccctagc actaggcaaa agcaatttaa tgccaccaca   2280
attccagaaa atgacataga gaagactgac ccttggtttg cacacagaac acctatgcct   2340
aaaatacaaa atgtctcctc tagtgatttg ttgatgctct gcgacagag tcctactcca   2400 catgggctat ccttatctga tctccaagaa gccaaatatg agacttttc tgatgatcca   2460 tcacctggag caatagacag taataacagc ctgtctgaaa tgacacactt caggccacag   2520
ctccatcaca gtggggacat ggtatttacc cctgagtcag gcctccaatt aagattaaat   2580
gagaaactgg ggacaactgc agcaacagag ttgaagaaac ttgatttcaa agtttctagt   2640
```

```
acatcaaata atctgatttc aacaattcca tcagacaatt tggcagcagg tactgataat      2700
acaagttcct taggacccccc aagtatgcca gttcattatg atagtcaatt agataccact      2760
ctatttggca aaaagtcatc tccccttact gagtctggtg gacctctgag cttgagtgaa      2820
gaaaataatg attcaaagtt gttagaatca ggtttaatga atagccaaga aagttcatgg      2880
ggaaaaaatg tatcgtcaac agagagtggt aggttattta aagggaaaag agctcatgga      2940
cctgctttgt tgactaaaga taatgcctta ttcaaagtta gcatctcttt gttaaagaca      3000
aacaaaactt ccaataattc agcaactaat agaaagactc acattgatgg cccatcatta      3060
ttaattgaga atagtccatc agtctggcaa aatatattag aaagtgacac tgagtttaaa      3120
aaagtgacac ctttgattca tgacagaatg cttatggaca aaaatgctac agctttgagg      3180
ctaaatcata tgtcaaataa aactacttca tcaaaaaaca tggaaatggt ccaacagaaa      3240
aaagagggcc ccattccacc agatgcacaa aatccagata tgtcgttctt taagatgcta      3300
ttcttgccag aatcagcaag gtggatacaa aggactcatg gaaagaactc tctgaactct      3360
gggcaaggcc ccagtccaaa gcaattagta tccttaggac cagaaaaatc tgtggaaggt      3420
cagaatttct tgtctgagaa aaacaaagtg gtagtaggaa agggtgaatt tacaaaggac      3480
gtaggactca aagagatggt ttttccaagc agcagaaacc tatttcttac taacttggat      3540
aatttacatg aaaataatac acacaatcaa gaaaaaaaaa ttcaggaaga aatagaaaag      3600
aaggaaacat taatccaaga gaatgtagtt ttgcctcaga tacatacagt gactggcact      3660
aagaatttca tgaagaacct tttcttactg agcactaggc aaaatgtaga aggttcatat      3720 gacgggcat atgctccagt acttcaagat tttaggtcat taaatgattc aacaaataga      3780
acaaagaaac acacagctca tttctcaaaa aaggggagg aagaaaactt ggaaggcttg      3840
ggaaatcaaa ccaagcaaat tgtagagaaa tatgcatgca ccacaaggat atctcctaat      3900
acaagccagc agaattttgt cacgcaacgt agtaagagag cttttgaaaca attcagactc      3960 ccactagaag aaacagaact tgaaaaaagg ataattgtgg atgacacctc aacccagtgg      4020
tccaaaaaca tgaaacattt gaccccgagc accctcacac agatagacta caatgagaag      4080
gagaaagggg ccattactca gtctcccttta tcagattgcc ttacgaggag tcatagcatc      4140
cctcaagcaa atagatctcc attacccatt gcaaaggtat catcatttcc atctattaga      4200
cctatatatc tgaccagggt cctattccaa gacaactctt ctcatcttcc agcagcatct      4260
tatagaaaga aagattctgg ggtccaagaa agcagtcatt tcttacaagg agccaaaaaa      4320
aataaccttt ctttagccat tctaaccttg gagatgactg tgatcaaag agaggttggc      4380 tccctgggga caagtgccac aaattcagtc acatacaaga aagttgagaa cactgttctc      4440
ccgaaaccag acttgcccaa aacatctggc aaagttgaat tgcttccaaa agttcacatt      4500
tatcagaagg acctattccc tacggaaact agcaatgggt ctcctggcca tctggatctc      4560
gtggaaggga gccttcttca gggaacagag ggagcgatta gtggaatga agcaaacaga      4620 cctggaaaag ttcccttttct gagagtagca acagaaagct ctgcaaagac tccctccaag      4680
ctattggatc ctcttgcttg ggataaccac tatggtactc agataccaaa agaagagtgg      4740
aaatcccaag agaagtcacc agaaaaaaca gcttttaaga aaaaggatac cattttgtcc      4800
ctgaacgctt gtgaaagcaa tcatgcaata gcagcaataa atgagggaca aaataagccc      4860
gaaatagaag tcacctgggc aaagcaaggt aggactgaaa ggctgtgctc tcaaaaccca      4920
ccagtcttga aacgccatca acgggaaata actcgtacta ctcttcagtc agatcaagag      4980
gaaattgact atgatgatac catatcagtt gaaatgaaga aggaagattt tgacatttat      5040
```

-continued

```
gatgaggatg aaaatcagag cccccgcagc tttcaaaaga aaacacgaca ctatttatt     5100
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagccctt ataccgtgga gaactaaatg aacatttggg actcctgggg    5280
ccatatataa gagcagaagt tgaagataat atcatggtaa ctttcagaaa tcaggcctct    5340
cgtccctatt ccttctattc tagccttatt tcttatgagg aagatcagag gcaaggagca    5400
gaacctagaa aaaactttgt caagcctaat gaaaccaaaa cttacttttg gaaagtgcaa    5460
catcatatgg cacccactaa agatgagttt gactgcaaag cctgggctta tttctctgat    5520
gttgacctgg aaaaagatgt gcactcaggc ctgattggac cccttctggt ctgccacact    5580
aacacactga accctgctca tgggagacaa gtgacagtac aggaatttgc tctgtttttc    5640
accatctttg atgagaccaa aagctggtac ttcactgaaa atatggaaag aaactgcagg    5700
gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaagaggag tataaaatgg cactgtacaa tctctatcca    5940
ggtgtttttg agacagtgga atgttacca tccaaagctg gaatttggcg ggtggaatgc    6000
cttattggcg agcatctaca tgctgggatg agcacctttt ttctggtgta cagcaataag    6060
tgtcagactc ccctgggaat ggcttctgga cacattagat tttttcagat tacagcttca    6120
ggacaatatg gacagtgggc cccaaagctg gccagacttc attattccgg atcaatcaat    6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg ggataaaaca atatttttt    6420
aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact ccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840
aaggttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctactga                          6999
```

<210> SEQ ID NO 2
<211> LENGTH: 2332
<212> TYPE: PRT
<213> ORGANISM: Human

<400> SEQUENCE: 2

Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro

-continued

```
            20                  25                  30
Arg Val Pro Lys Ser Phe Pro Phe Asn Thr Ser Val Val Tyr Lys Lys
            35                  40                  45

Thr Leu Phe Val Glu Phe Thr Val His Leu Phe Asn Ile Ala Lys Pro
            50                  55                  60

Arg Pro Pro Trp Met Gly Leu Leu Gly Pro Thr Ile Gln Ala Glu Val
 65                  70                  75                  80

Tyr Asp Thr Val Ile Thr Leu Lys Asn Met Ala Ser His Pro Val
                    85                  90                  95

Ser Leu His Ala Val Gly Val Ser Tyr Trp Lys Ala Ser Glu Gly Ala
                   100                 105                 110

Glu Tyr Asp Asp Gln Thr Ser Gln Arg Glu Lys Glu Asp Asp Lys Val
                   115                 120                 125

Phe Pro Gly Gly Ser His Thr Tyr Val Trp Gln Val Leu Lys Glu Asn
            130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                    165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
            210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                    245                 250                 255

Val Ile Gly Met Gly Thr Thr Pro Glu Val His Ser Ile Phe Leu Glu
                    260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                    325                 330                 335

Met Lys Asn Asn Glu Glu Ala Glu Asp Tyr Asp Asp Asp Leu Thr Asp
                    340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
            370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                    405                 410                 415

Gln Arg Ile Gly Arg Lys Tyr Lys Lys Val Arg Phe Met Ala Tyr Thr
                    420                 425                 430

Asp Glu Thr Phe Lys Thr Arg Glu Ala Ile Gln His Glu Ser Gly Ile
            435                 440                 445
```

-continued

```
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
    690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
        755                 760                 765
Thr Asp Pro Trp Phe Ala His Arg Thr Pro Met Pro Lys Ile Gln Asn
    770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
        835                 840                 845
Phe Thr Pro Glu Ser Gly Leu Gln Leu Arg Leu Asn Glu Lys Leu Gly
    850                 855                 860
```

```
Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
    915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
        980                 985                 990

Val Ser Ile Ser Leu Leu Lys Thr Asn Lys Thr Ser Asn Asn Ser Ala
    995                 1000                1005

Thr Asn Arg Lys Thr His Ile Asp Gly Pro Ser Leu Leu Ile Glu Asn
    1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
            1045                1050                1055

Thr Ala Leu Arg Leu Asn His Met Ser Asn Lys Thr Thr Ser Ser Lys
        1060                1065                1070

Asn Met Glu Met Val Gln Gln Lys Lys Glu Gly Pro Ile Pro Pro Asp
    1075                1080                1085

Ala Gln Asn Pro Asp Met Ser Phe Phe Lys Met Leu Phe Leu Pro Glu
    1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
            1125                1130                1135

Ser Val Glu Gly Gln Asn Phe Leu Ser Glu Lys Asn Lys Val Val Val
        1140                1145                1150

Gly Lys Gly Glu Phe Thr Lys Asp Val Gly Leu Lys Glu Met Val Phe
    1155                1160                1165

Pro Ser Ser Arg Asn Leu Phe Leu Thr Asn Leu Asp Asn Leu His Glu
1170                1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
            1205                1210                1215

Val Thr Gly Thr Lys Asn Phe Met Lys Asn Leu Phe Leu Leu Ser Thr
        1220                1225                1230

Arg Gln Asn Val Glu Gly Ser Tyr Glu Gly Ala Tyr Ala Pro Val Leu
    1235                1240                1245

Gln Asp Phe Arg Ser Leu Asn Asp Ser Thr Asn Arg Thr Lys Lys His
    1250                1255                1260

Thr Ala His Phe Ser Lys Lys Gly Glu Glu Glu Asn Leu Glu Gly Leu
1265                1270                1275                1280

Gly Asn Gln Thr Lys Gln Ile Val Glu Lys Tyr Ala Cys Thr Thr Arg
```

-continued

```
                1285                1290                1295
Ile Ser Pro Asn Thr Ser Gln Gln Asn Phe Val Thr Gln Arg Ser Lys
        1300                1305                1310

Arg Ala Leu Lys Gln Phe Arg Leu Pro Leu Glu Glu Thr Glu Leu Glu
        1315                1320                1325

Lys Arg Ile Ile Val Asp Asp Thr Ser Thr Gln Trp Ser Lys Asn Met
    1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
            1365                1370                1375

Ser His Ser Ile Pro Gln Ala Asn Arg Ser Pro Leu Pro Ile Ala Lys
        1380                1385                1390

Val Ser Ser Phe Pro Ser Ile Arg Pro Ile Tyr Leu Thr Arg Val Leu
    1395                1400                1405

Phe Gln Asp Asn Ser Ser His Leu Pro Ala Ala Ser Tyr Arg Lys Lys
1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
            1445                1450                1455

Arg Glu Val Gly Ser Leu Gly Thr Ser Ala Thr Asn Ser Val Thr Tyr
        1460                1465                1470

Lys Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys Asp
        1490                1495                1500

Leu Phe Pro Thr Glu Thr Ser Asn Gly Ser Pro Gly His Leu Asp Leu
1505                1510                1515                1520

Val Glu Gly Ser Leu Leu Gln Gly Thr Glu Gly Ala Ile Lys Trp Asn
            1525                1530                1535

Glu Ala Asn Arg Pro Gly Lys Val Pro Phe Leu Arg Val Ala Thr Glu
        1540                1545                1550

Ser Ser Ala Lys Thr Pro Ser Lys Leu Leu Asp Pro Leu Ala Trp Asp
    1555                1560                1565

Asn His Tyr Gly Thr Gln Ile Pro Lys Glu Glu Trp Lys Ser Gln Glu
        1570                1575                1580

Lys Ser Pro Glu Lys Thr Ala Phe Lys Lys Lys Asp Thr Ile Leu Ser
1585                1590                1595                1600

Leu Asn Ala Cys Glu Ser Asn His Ala Ile Ala Ala Ile Asn Glu Gly
            1605                1610                1615

Gln Asn Lys Pro Glu Ile Glu Val Thr Trp Ala Lys Gln Gly Arg Thr
        1620                1625                1630

Glu Arg Leu Cys Ser Gln Asn Pro Pro Val Leu Lys Arg His Gln Arg
    1635                1640                1645

Glu Ile Thr Arg Thr Thr Leu Gln Ser Asp Gln Glu Glu Ile Asp Tyr
    1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
            1685                1690                1695

His Tyr Phe Ile Ala Ala Val Glu Arg Leu Trp Asp Tyr Gly Met Ser
        1700                1705                1710
```

```
Ser Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe Thr
1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
                1765                1770                1775

Asn Gln Ala Ser Arg Pro Tyr Ser Phe Tyr Ser Ser Leu Ile Ser Tyr
            1780                1785                1790

Glu Glu Asp Gln Arg Gln Gly Ala Glu Pro Arg Lys Asn Phe Val Lys
    1795                1800                1805

Pro Asn Glu Thr Lys Thr Tyr Phe Trp Lys Val Gln His His Met Ala
1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
                1845                1850                1855

Val Cys His Thr Asn Thr Leu Asn Pro Ala His Gly Arg Gln Val Thr
            1860                1865                1870

Val Gln Glu Phe Ala Leu Phe Phe Thr Ile Phe Asp Glu Thr Lys Ser
    1875                1880                1885

Trp Tyr Phe Thr Glu Asn Met Glu Arg Asn Cys Arg Ala Pro Cys Asn
    1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
                1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe Glu
    1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
                2005                2010                2015

Tyr Ser Asn Lys Cys Gln Thr Pro Leu Gly Met Ala Ser Gly His Ile
            2020                2025                2030

Arg Asp Phe Gln Ile Thr Ala Ser Gly Gln Tyr Gly Gln Trp Ala Pro
    2035                2040                2045

Lys Leu Ala Arg Leu His Tyr Ser Gly Ser Ile Asn Ala Trp Ser Thr
    2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
                2085                2090                2095

Tyr Ile Ser Gln Phe Ile Ile Met Tyr Ser Leu Asp Gly Lys Lys Trp
            2100                2105                2110

Gln Thr Tyr Arg Gly Asn Ser Thr Gly Thr Leu Met Val Phe Phe Gly
    2115                2120                2125
```

-continued

```
Asn Val Asp Ser Ser Gly Ile Lys His Asn Ile Phe Asn Pro Pro Ile
    2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
                2165                2170                2175

Pro Leu Gly Met Glu Ser Lys Ala Ile Ser Asp Ala Gln Ile Thr Ala
            2180                2185                2190

Ser Ser Tyr Phe Thr Asn Met Phe Ala Thr Trp Ser Pro Ser Lys Ala
        2195                2200                2205

Arg Leu His Leu Gln Gly Arg Ser Asn Ala Trp Arg Pro Gln Val Asn
    2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
                2245                2250                2255

Val Lys Glu Phe Leu Ile Ser Ser Ser Gln Asp Gly His Gln Trp Thr
            2260                2265                2270

Leu Phe Phe Gln Asn Gly Lys Val Lys Val Phe Gln Gly Asn Gln Asp
        2275                2280                2285

Ser Phe Thr Pro Val Val Asn Ser Leu Asp Pro Pro Leu Leu Thr Arg
    2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
                2325                2330

<210> SEQ ID NO 3
<211> LENGTH: 17
<212> TYPE: PRT
<213> ORGANISM: Human

<400> SEQUENCE: 3

Glu Gly Ala Ser Tyr Leu Asp His Thr Phe Pro Ala Glu Lys Met Asp
  1               5                  10                  15

Asp

<210> SEQ ID NO 4
<211> LENGTH: 17
<212> TYPE: PRT
<213> ORGANISM: Human

<400> SEQUENCE: 4

Glu Gly Ala Glu Tyr Asp Asp Gln Thr Ser Gln Arg Glu Lys Glu Asp
  1               5                  10                  15

Asp

<210> SEQ ID NO 5
<211> LENGTH: 17
<212> TYPE: PRT
<213> ORGANISM: Porcine

<400> SEQUENCE: 5

Glu Gly Ala Glu Tyr Glu Asp His Thr Ser Gln Arg Glu Lys Glu Asp
  1               5                  10                  15

Asp
```

```
<210> SEQ ID NO 6
<211> LENGTH: 17
<212> TYPE: PRT
<213> ORGANISM: Murine

<400> SEQUENCE: 6

Glu Gly Asp Glu Tyr Glu Asp Gln Thr Ser Gln Met Glu Lys Glu Asp
 1               5                  10                  15
Asp

<210> SEQ ID NO 7
<211> LENGTH: 17
<212> TYPE: PRT
<213> ORGANISM: Canine

<400> SEQUENCE: 7

Glu Gly Ala Glu Tyr Glu Asp Gln Thr Ser Gln Lys Glu Lys Glu Asp
 1               5                  10                  15
Asp
```

RECOMBINANT FACTOR VIII HAVING INCREASED SPECIFIC ACTIVITY

This application is a national stage application under 35 U.S.C. §371 from PCT Application No. PCT/US2004/040234, filed Dec. 2, 2004, which claims the benefit of U.S. Provisional Patent Application Ser. No. 60/526,664, filed Dec. 3, 2003, which is hereby incorporated by reference in its entirety.

The present invention was made with funding received from the National Institutes of Health under grants HL 38199 and HL 30616. The U.S. government may retain certain rights in this invention.

FIELD OF THE INVENTION

The present invention relates to recombinant factor VIII having a specific activity that is higher than that of the corresponding wild-type factor VIII. The present invention also relates to methods of making and using the recombinant factor VIII.

BACKGROUND OF THE INVENTION

Factor VIII, a plasma protein that participates in the blood coagulation cascade, is decreased or defective in individuals with hemophilia A. Factor VIII functions as a cofactor for the serine protease factor IXa in the surface-dependent conversion of zymogen factor X to the serine protease, factor Xa (Davie, E. W., *Thromb. Haemost.* 74:1-6 (1995); Lollar, P., *Adv. Exp. Med. Biol.* 386:3-17 (1995)). Deficiency of factor VIII activity results in a marked reduction of factor IXa activity and in the subsequent rates of factor Xa generated during the propagation phase of coagulation.

Factor VIII is synthesized as an ~300-kDa single chain precursor protein (Wood et al., *Nature* 312:330-337 (1984); Toole et al., *Nature* 312:342-347 (1984)) with domain structure A1-A2-B-A3-C1-C2 (Vehar et al., *Nature* 312:337-342 (1984)). Factor VIII is processed to a series of divalent metal ion-linked heterodimers (Fass et al., *Blood* 59:594-600 (1982); Andersson et al., *Proc. Natl. Acad. Sci. U.S.A.* 83:2979-2983 (1986); Fay et al., *Biochim. Biophys. Acta* 871:268-278 (1986)) by cleavage at the B-A3 junction, generating a heavy chain (HC[1]) minimally represented by the A1-A2 domains; and a light chain (LC) consisting of the A3-C1-C2 domains. The A domains of factor VIII share homology with the A domains of factor V and the copper-binding protein, ceruloplasmin (Church et al., *Proc. Natl. Acad. Sci. U.S.A.* 81:6934-6937 (1984)). One mol of copper has been identified in factor VIII (Bihoreau et al., *Eur. J. Biochem.* 220:41-48 (1994); Tagliavacca et al., *J. Biol. Chem.* 272:27428-27434 (1997)).

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classic definition of factor VIII, in fact, is that substance present in normal blood plasma that corrects the clotting defect in plasma derived from individuals with hemophilia A.

The development of antibodies ("inhibitors" or "inhibitory antibodies") that inhibit the activity of factor VIII is a serious complication in the management of patients with hemophilia. Autoantibodies develop in approximately 20% of patients with hemophilia A in response to therapeutic infusions of factor VIII. In previously untreated patients with hemophilia A who develop inhibitors, the inhibitor usually develops within one year of treatment. Additionally, autoantibodies that inactivate factor VIII occasionally develop in individuals with previously normal factor VIII levels. If the inhibitor titer is low enough, patients can be managed by increasing the dose of factor VIII. However, often the inhibitor titer is so high that it cannot be overwhelmed by factor VIII. An alternative strategy is to bypass the need for factor VIII during normal hemostasis using factor IX complex preparations (for example, KONYNE®, Proplex®) or recombinant human factor VIIa. Additionally, since porcine factor VIII usually has substantially less reactivity with inhibitors than human factor VIII, a partially purified porcine factor VIII preparation (HYATE:C®) is used. Many patients who have developed inhibitory antibodies to human factor VIII have been successfully treated with porcine factor VIII and have tolerated such treatment for long periods of time. However, administration of porcine factor VIII is not a complete solution because inhibitors may develop to porcine factor VIII after one or more infusions.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contain a significant level of antigenic proteins; a monoclonal antibody-purified factor VIII that has lower levels of antigenic impurities and viral contamination; and recombinant human factor VIII, clinical trials for which are underway. Unfortunately, human factor VIII is unstable at physiologic concentrations and pH, is present in blood at an extremely low concentration (0.2 µg/ml plasma), and has low specific clotting activity.

Hemophiliacs require daily replacement of factor VIII to prevent bleeding and the resulting deforming hemophilic arthropathy. However, supplies have been inadequate and problems in therapeutic use occur due to difficulty in isolation and purification, immunogenicity, and the necessity of removing the AIDS and hepatitis infectivity risk. The use of recombinant human factor VIII or partially-purified porcine factor VIII will not resolve all the problems.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to cause production of inhibitory antibodies; and a factor VIII molecule that evades immune detection in patients who have already acquired antibodies to human factor VIII.

The present invention is directed to overcoming these and other deficiencies in the art.

SUMMARY OF THE INVENTION

A first aspect of the present invention relates to a recombinant factor VIII having increased specific (or pro-coagulant) activity as compared to wild-type factor VIII. The recombinant factor VIII includes a point mutation in or near at least one calcium binding site of a wild-type factor VIII.

A second aspect of the present invention also relates to a pharmaceutical composition including the recombinant factor VIII of the present invention.

A third aspect of the present invention relates to an isolated nucleic acid molecule that encodes the recombinant factor VIII of the present invention.

A fourth aspect of the present invention relates to a recombinant DNA expression system that includes an isolated DNA molecule of the present invention, which expression system encodes a recombinant factor VIII.

A fifth aspect of the present invention relates to a host cell including an isolated nucleic acid molecule encoding the recombinant factor VIII of the present invention.

A sixth aspect of the present invention relates to a method of making a recombinant factor VIII having increased specific activity compared to that of a wild-type factor VIII. This method involves growing a host cell including an isolated nucleic acid molecule encoding the recombinant factor VIII of the present invention. The host cell is grown under conditions whereby the host cell expresses the recombinant factor VIII. Thereafter, the recombinant factor VIII is isolated.

A seventh aspect of the present invention relates to a method of making a recombinant factor VIII having increased specific activity compared to that of a wild-type factor VIII. This method involves altering the amino acid sequence of a wild-type factor VIII to yield a recombinant factor VIII. Alteration of the amino acid sequence of the wild-type factor VIII can include, for example, introducing at least one point mutation in or near at least one calcium binding site of the wild-type factor VIII. Thereafter, using protein analysis techniques well-known in the art, a determination can be made as to whether the recombinant factor VIII has increased specific activity compared to that of the wild-type factor VIII.

An eighth aspect of the present invention relates to a method of treating an animal for hemophilia A. This method involves administering to an animal exhibiting hemophilia A an effective amount of the recombinant factor VIII of the present invention, whereby the animal exhibits effective blood clotting following vascular injury.

Applicants have surprisingly identified that the recombinant factor VIII of the present invention can differ in specific activity from the wild-type factor VIII. Factor VIII proteins having greater procoagulant activity from wild-type factor VIII are useful in treatment of hemophilia because lower dosages will be required to correct a patient's factor VIII deficiency. This will not only reduce medical expense for both the patient and the insurer, but also reduce the likelihood of developing an immune response to the factor VIII (because less antigen is administered).

BRIEF DESCRIPTION OF THE DRAWINGS

FIG. 3A: High activity species include wild type (open circles), E113A (open triangles), and E115A (open squares). FIG. 3B: Moderate activity species include E122A (open circles), E122D (open triangles), E124A (open squares), and D126A (closed circles). FIG. 3C: Low activity species include E110A (open circles), E110D (open triangles), D116A (open squares), and D125A (closed circles). Lines were drawn from the curve fit according to a single-site binding model as described in Example 4 (infra).

FIG. 4A: High activity species include wild type (open circles), E113A (open triangles), and E115A (open squares). FIG. 4B: Moderate activity species include E122A (open circles), E122D (open triangles), E124A (open squares), and D126A (closed circles). FIG. 4C: Low activity species include E110A (open circles), E110D (open triangles), D116A (open squares), and D125A (closed circles). Lines were drawn from the curve fit according to a single-site binding model as described in Example 4 (infra).

FIG. 5 shows the sequence alignments of human factor V (SEQ ID NO:3) and human factor VIII (SEQ ID NO:4, which corresponds to residues 110-126 of SEQ ID NO:2). Residues are indicated by the single letter designation. Acidic residues are in bold typeface. Matched acidic residues are underlined.

FIG. 6 shows the sequence alignments of residues 110-126 of the peptide sequences of factor VIII from human (SEQ ID NO:4), porcine (SEQ ID NO:5), murine (SEQ ID NO:6), and canine (SEQ ID NO:7). Amino acid residues are indicated using the single letter designation. Acidic residues are in bold and those homologous to factor V (SEQ ID NO:3) are underlined. E113 is conserved in all species.

FIG. 9A: Titration of factor IXa with factor VIIIa. FIG. 9B: Titration of factor Xase complex with factor X.

FIG. 10A: Titration of factor IXa with factor VIIIa. FIG. 10B: Titration of factor Xase complex with factor X.

DETAILED DESCRIPTION OF THE INVENTION

Figure 1:
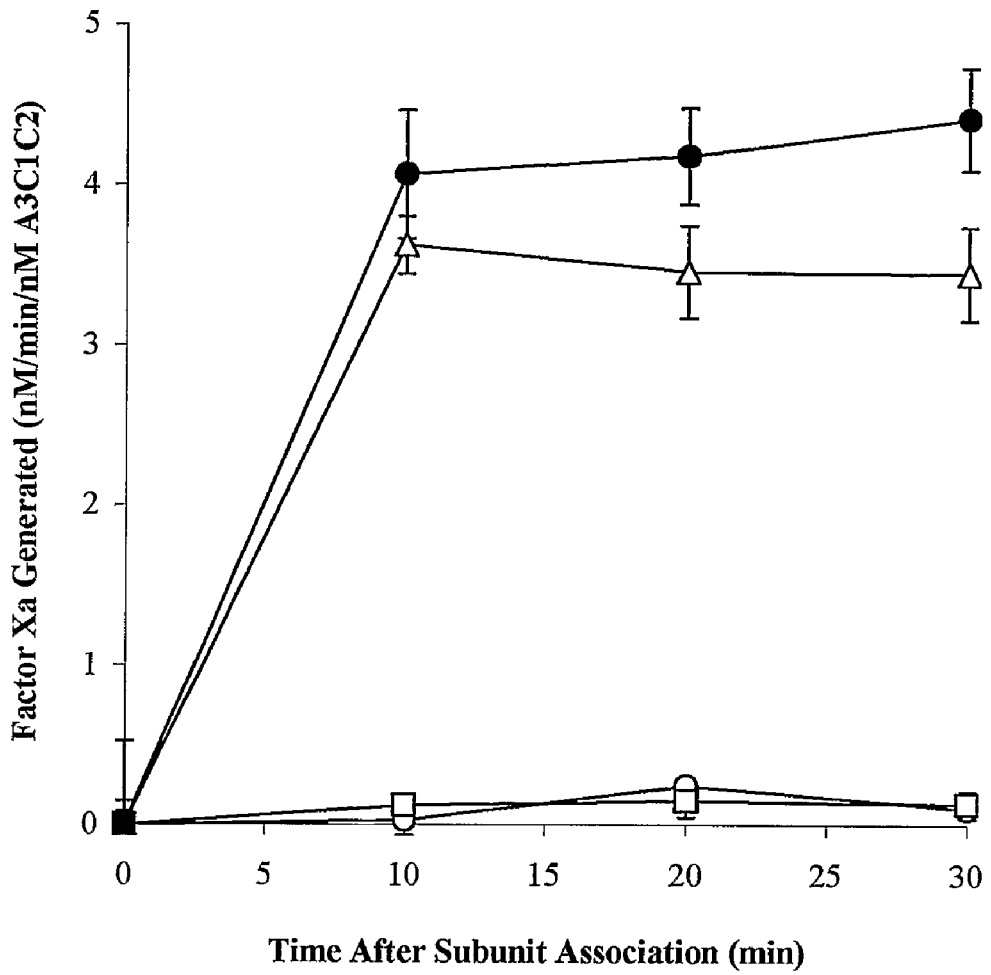
FIG. 1 is a graph showing the effect of pre-incubation with $Ca^{2+}$ on factor VIIIa reconstitution from isolated subunits. Factor VIII subunits (A1/A3-C1-C2 and A2) were separately pre-incubated with 3 mM $Ca^{2+}$ or 0.1 mM EDTA for 18 hours. After mixing the pre-incubated A1/A3-C1-C2 and A2, reconstituted factor VIIIa activity was measured by a factor Xa generation assay as described in Example 2 (infra). Mixtures were A1/A3-C1-C2 pre-incubated with $Ca^{2+}$ plus A2 pre-incubated with $Ca^{2+}$ (closed circles), A1/A3-C1-C2 pre-incubated with EDTA plus A2 pre-incubated with $Ca^{2+}$ (squares), A1/A3-C1-C2 pre-incubated with $Ca^{2+}$ plus A2 pre-incubated with EDTA (triangles), and A1/A3-C1-C2 pre-incubated with EDTA plus A2 pre-incubated EDTA (open circles). Each point represents the average of four determinations.

The present invention relates to a recombinant factor VIII having increased specific (or pro-coagulant) activity as compared to wild-type factor VIII. The recombinant factor VIII includes a point mutation in or near at least one calcium binding site of a wild-type factor VIII. As used herein, "in or near" means within about five amino acid residues from a residue that directly interacts with $Ca^{2+}$ or $Mn^{2+}$ ions.

The recombinant factor VIII of the present invention can be prepared by modifying the amino acid sequence of a wild-type factor VIII or a mutant factor VIII that has otherwise been modified to affect other properties of the factor VIII, such as antigenicity, circulating half-life, protein secretion, affinity for factor IXa and/or factor X, altered factor VIII-inactivation cleavage sites, stability of the activated factor VIII form, immunogenicity, shelf-life, etc.

Suitable wild-type factor VIII that can be modified in accordance with the present invention can be from various animals including, without limitation, mammals such as humans (see, e.g., GenBank Accession Nos. AAA52484 (amino acid) and K01740 (nucleotide); and GenBank Accession Nos. CAD97566 (amino acid) and AX746360 (nucleotide), which are hereby incorporated by reference in their entirety), rats (see, e.g., GenBank Accession Nos. AAQ21580 (amino acid) and AY362193 (nucleotide), which are hereby incorporated by reference in their entirety), mice (see, e.g., GenBank Accession Nos. AAA37385 (amino acid) and L05573 (nucleotide), which are hereby incorporated by reference in their entirety), guinea pigs, dogs (see, e.g., GenBank Accession Nos. AAB87412 (amino acid) and AF016234 (nucleotide); and GenBank Accession Nos. AAC05384 (amino acid) and AF049489 (nucleotide), which are hereby incorporated by reference in their entirety), cats, monkeys, chimpanzees (see, e.g., GenBank Accession Nos. XP_529212 (amino acid) and XM_529212 (nucleotide), which are hereby incorporated by reference in their entirety), orangutans, cows, horses, sheep, pigs (see, e.g., GenBank Accession Nos. NP_999332 (amino acid) and NM_214167 (nucleotide), which are hereby incorporated by reference in their entirety), goats, rabbits, and chickens. These and other sequences are also available electronically via the Haemophilia A Mutation, Structure, Test and Resource Site (or HAMSTeRS), which further provides an alignment of human, porcine, murine, and canine factor VIII proteins. Thus, the conservation and homology among mammalian factor VIII proteins is well known.

By way of example, the human factor VIII cDNA nucleotide and predicted amino acid sequences are shown below in SEQ ID NOs: 1 and 2, respectively. Human factor VIII is synthesized as an approximately 300 kDa single chain protein with internal sequence homology that defines the "domain" sequence $NH_2$-A1-A2-B-A3-C1-C2-COOH. In a factor VIII molecule, a "domain," as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO: 2):

- A1, residues $Ala_1$-$Arg_{372}$;
- A2, residues $Ser_{373}$-$Arg_{740}$;
- B, residues $Ser_{741}$-$Arg_{1648}$;
- A3, residues $Ser_{1690}$-$Ile_{2032}$;
- C1, residues $Arg_{2033}$-$Asn_{2172}$; and
- C2, residues $Ser_{2173}$-$Tyr_{2332}$.

The A3-C1-C2 sequence includes residues $Ser_{1690}$-$Tyr_{2332}$. The remaining sequence, residues $Glu_{1649}$-$Arg_{1689}$, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

The gene encoding the wild-type human factor VIII has a nucleotide sequence of SEQ ID NO:1, as follows:

```
gccaccagaagatactacctgggtgcagtggaactgtcatgggactatat
gcaaagtgatctcggtgagctgcctgtggacgcaagatttcctcctagag
tgccaaaatcttttccattcaacacctcagtcgtgtacaaaaagactctg
tttgtagaattcacggatcaccttttcaacatcgctaagccaaggccacc
ctggatgggtctgctaggtcctaccatccaggctgaggtttatgatacag
tggtcattacacttaagaacatggcttcccatcctgtcagtcttcatgct
gttggtgtatcctactggaaagcttctgagggagctgaatatgatgatca
gaccagtcaaagggagaaagaagatgataaagtcttccctggtggaagcc
atacatatgtctggcaggtcctgaaagagaatggtccaatggcctctgac
ccactgtgccttacctactcatatctttctcatgtggacctggtaaaaga
cttgaattcaggcctcattggagccctactagtatgtagagaagggagtc
tggccaaggaaaagacacagaccttgcacaaatttatactacttttttgct
gtatttgatgaagggaaaagttggcactcagaaacaaagaactccttgat
gcaggatagggatgctgcatctgctcgggcctggcctaaaatgcacacag
tcaatggttatgtaaacaggtctctgccaggtctgattggatgccacagg
aaatcagtctattggcatgtgattggaatgggcaccactcctgaagtgca
ctcaatattcctcgaaggtcacacatttcttgtgaggaaccatcgccagg
cgtccttggaaatctcgccaataactttccttactgctcaaacactcttg
atggaccttggacagtttctactgttttgtcatatctcttcccaccaaca
tgatggcatggaagcttatgtcaaagtagacagctgtccagaggaacccc
aactacgaatgaaaataatgaagaagcggaagactatgatgatgatctt
actgattctgaaatggatgtggtcaggtttgatgatgacaactctccttc
ctttatccaaattcgctcagttgccaagaagcatcctaaaacttgggtac
attacattgctgctgaagaggaggactgggactatgctcccttagtcctc
gcccccgatgacagaagttataaaagtcaatatttgaacaatggccctca
gcggattggtaggaagtacaaaaaagtccgatttatggcatacacagatg
aaacctttaagactcgtgaagctattcagcatgaatcaggaatcttggga
cctttactttatgggaagttggagacacactgttgattatatttaagaa
tcaagcaagcagaccatataacatctaczctcacggaatcactgatgtcc
gtcctttgtattcaaggagattaccaaaaggtgtaaaacatttgaaggat
tttccattctgccaggagaaatattcaaatataaatggacagtgactgta
```

-continued gaagatgggccaactaaatcagatcctcggtgcctgacccgctattactc
tagtttcgttaatatggagagagatctagcttcaggactcattggccctc
tcctcatctgctacaaagaatctgtagatcaaagaggaaaccagataatg
tcagacaagaggaatgtcatcctgttttctgtatttgatgagaaccgaag
ctggtacctcacagagaatatacaacgctttctccccaatccagctggag
tgcagcttgaggatccagagttccaagcctccaacatcatgcacagcatc
aatggctatgttttgatagtttgcagttgtcagtttgtttgcatgaggt
ggcatactggtacattctaagcattggagcacagactgacttcctttctg
tcttcttctctggatataccttcaaacacaaaatggtctatgaagacaca
ctcaccctattccccattctcaggagaaactgtcttcatgtcgatggaaaa
cccaggtctatggattctggggtgccacaactcagactttcggaacagag
gcatgaccgccttactgaaggtttctagttgtgacaagaacactggtgat
tattacgaggacagttatgaagatatttcagcatacttgctgagtaaaaa
caatgccattgaaccaagaagcttctcccagaattcaagacaccctagca
ctaggcaaaagcaatttaatgccaccacaattccagaaaatgacatagag
aagactgacccttggtttgcacacagaacacctatgcctaaaatacaaaa
tgtctcctctagtgatttgttgatgctcttgcgacagagtcctactccac
atgggctatccttatctgatctccaagaagccaaatatgagactttttct
gatgatccatcacctggagcaatagacagtaataacagcctgtctgaaat
gacacacttcaggccacagctccatcacagtggggacatggtatttaccc
ctgagtcaggcctccaattaagattaaatgagaaactggggacaactgca
gcaacagagttgaagaaacttgatttcaaagtttctagtacatcaaataa
tctgatttcaacaattccatcagacaatttggcagczaggtactgataat
acaagttccttaggaccccaagtatgccagttcattatgatagtcaatt
agataccactctatttggcaaaaagtcatctcccccttactgagtctggtg
gacctctgagcttgagtgaagaaaataatgattcaaagttgttagaatca
ggtttaatgaatagccaagaaagttcatggggaaaaaatgtatcgtcaac
agagagtggtaggttatttaaagggaaaagagctcatggacctgctttgt
tgactaaagataatgccttattcaaagttagcatctctctttgttaaagaca
aacaaaacttccaataattcagcaactaatagaaagactcacattgatgg
cccatcattattaattgagaatagtccatcagtctggcaaaatatattag
aaagtgacactgagtttaaaaaagtgacacctttgattcatgacagaatg
cttatgacaaaaatgctacagctttgaggctaaatcatatgtcaaataa
aactacttcatcaaaaaacatggaaatggtccaacagaaaaagagggcc
ccattccaccagatgcacaaaatccagatatgtcgttctttaagatgcta
ttcttgccagaatcagcaaggtggatacaaaggactcatggaagaactc
tctgaactctgggcaaggcccagtccaaagcaattagtatccttaggac
cagaaaaatctgtggaaggtcagaatttcttgtctgagaaaaacaaagtg
gtagtaggaaagggtgaatttacaaaggacgtaggactcaaagagatggt
ttttccaagcagcagaaacctatttcttactaacttggataatttacatg -continued aaaataatacacacaatcaagaaaaaaaaattcaggaagaaatagaaaag
aaggaaacattaatccaagagaatgtagttttgcctcagatacatacagt
gactggcactaagaatttcatgaagaaccttttcttactgagcactaggc
aaaatgtagaaggttc&tatgacggggcatatgctccagtacttcaagat
tttaggtcattaaatgattcaacaaatagaacaaagaaacacacagctca
tttctcaaaaaaggggaggaagaaaacttggaaggcttgggaaatcaaa
ccaagcaaattgtagagaaatatgcatgcaccacaaggatatctcctaat
acaagccagcagaattttgtcacgcaacgtagtaagagagctttgaaaca
attcagactcccactagaagaaacagaacttgaaaaaaggataattgtgg
atgacacctcaacccagtggtccaaaaacatgaaacatttgaccccgagc
accctcacacagatagactacaatgagaaggagaaaggggccattactca
gtctcccttatcagattgccttacgaggagtcatagcatccctcaagcaa
atagatctccattacccattgcaaaggtatcatcatttccatctattaga
cctatatatctgaccagggtcctattccaagacaactcttctcatcttcc
agcagcatcttatagaaagaaagattctggggtccaagaaagcagtcatt
tcttacaaggagccaaaaaaaataaccctttctttagccattctaaccttg
gagatgactggtgatcaaagagaggttggctccctggggacaagtgccac
aaattcagtcacatacaagaaagttgagaacactgttctcccgaaaccag
acttgcccaaaacatctggcaaagttgaattgcttccaaaagttcacatt
tatcagaaggacctattccctacggaaactagcaatgggtctcctggcca
tctggatctcgtggaagggagccttcttcagggaacagagggagcgatta
agtggaatgaagcaaacagacctggaaaagttccctttctgagagtagca
acagaaagctctgcaaagactccctccaagctattggatcctcttgcttg
ggataaccactatggtactcagataccaaaagaagagtggaaatcccaag
agaagtcaccagaaaaaacagcttttaagaaaaaggataccattttgtcc
ctgaacgcttgtgaaagcaatcatgcaatagcagcaataaatgagggaca
aaataagcccgaaatagaagtcacctgggcaaagcaaggtaggactgaaa
ggctgtgctctcaaaacccaccagtcttgaaacgccatcaacgggaaata
actcgtactactcttcagtcagatcaagaggaaattgactatgatgatac
catatcagttgaaatgaagaaggaagattttgacatttatgatgaggatg
aaaatcagagccccgcagctttcaaaagaaaacacgacactattttatt
gctgcagtggagaggctctgggattatgggatgagtagctccccacatgt
tctaagaaacagggctcagagtggcagtgtccctcagttcaagaaagttg
ttttccaggaatttactgatggctcctttactcagcccttataccgtgga
gaactaaatgaacatttgggactcctggggcatatataagagcagaagt
tgaagataatatcatggtaacttcagaaatcaggcctctcgtccctatt
ccttctattctagccttatttcttatgaggaagatcagaggcaaggagca
gaacctagaaaaaactttgtcaagcctaatgaaaccaaaacttacttttg
gaaagtgcaacatcatatggcacccactaaagatgagtttgactgcaaag
cctgggcttatttctctgatgttgacctggaaaaagatgtgcactcaggc -continued

```
ctgattggaccccttctggtctgccacactaacacactgaaccctgctca
tgggagacaagtgacagtacaggaatttgctctgttttcaccatctttg
atgagaccaaaagctggtacttcactgaaaatatggaagaaactgcagg
gctccctgcaatatccagatggaagatcccacttttaaagagaattatcg
cttccatgcaatcaatggctacataatggatacactacctggcttagtaa
tggctcaggatcaaaggattcgatggtatctgctcagcatgggcagcaat
gaaaacatccattctattcatttcagtggacatgtgttcactgtacgaaa
aaaagaggagtataaaatggcactgtacaatctctatccaggtgttttg
agacagtggaaatgttaccatccaaagctggaatttggcgggtggaatgc
cttattggcgagcatctacatgctgggatgagcacacttttctggtgta
cagcaataagtgtcagactcccctgggaatggcttctggacacattagag
attttcagattacagcttcaggacaatatggacagtgggccccaaagctg
gccagacttcattattccggatcaatcaatgcctggagcaccaaggagcc
cttttcttggatcaaggtggatctgttggcaccaatgattattcacggca
tcaagacccagggtgcccgtcagaagttctccagcctctacatctctcag
tttatcatcatgtatagtcttgatgggaagaagtggcagacttatcgagg
aaattccactggaaccttaatggtcttctttggcaatgtggattcatctg
ggataaaacacaatattttaaccctccaattattgctcgatacatccgt
ttgcacccaactcattatagcattcgcagcactcttcgcatggagttgat
gggctgtgatttaaatagttgcagcatgccattgggaatggagagtaaag
caatatcagatgcacagattactgcttcatcctactttaccaatatgttt
gccacctggtctccttcaaaagctcgacttcacctccaagggaggagtaa
tgcctggagacctcaggtgaataatccaaaagagtggctgcaagtggact
tccagaagacaatgaaagtcacaggagtaactactcagggagtaaaatct
ctgcttaccagcatgtatgtgaaggagttcctcatctccagcagtcaaga
tggccatcagtggactctcttttttcagaatggcaaagtaaaggttttc
agggaaatcaagactccttcacacctgtggtgaactctctagacccaccg
ttactgactcgctaccttcgaattcacccccagagttgggtgcaccagat
tgccctgaggatggaggttctgggctgcgaggcacaggacctctactga
```

The wild-type human factor VIII encoded by SEQ ID NO:1 has an amino acid sequence of SEQ ID NO:2, as follows:

ATRRYYLGAVELSWDYMQSDLGELPVDARFPPRVPKSFPFNTSVVYKKTL
FVEFTVHLFNIAKPRPPWMGLLGPTIQAEVYDTVVITLKNMASHPVSLHA
VGVSYWKAS<u>EGAEYDDQTSQREKEDD</u>KVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR
KSVYWHVIGMGTTPEVHSIFLEGHTFLVRNHRQASLEISPITFLTAQTLL
MDLGQFLLFCHISSHQHDGMEAYVKVDSCPEEPQLRMKNNEEAEDYDDDL
TDSEMDVVRFDDDNSPSFIQIRSVAKKHPKTWVHYIAAEEEDWDYAPLVL
APDDRSYKSQYLNNGPQRIGRKYKKVRFMAYTDETFKTREAIQHESGILG
PLLYGEVGDTLLIIFKNQASRPYNIYPHGITDVRPLYSRRLPKGVKHLKD
FPILPGEIFKYKWTVTVEDGPTKSDPRCLTRYYSSFVNMERDLASGLIGP
LLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNR
GMTALLKVSSCDKNTGDYYEDSYEDISAYLLSKNNAIEPRSFSQNSRHPS
TRQKQFNATTIPENDIEKTDPWFAHRTPMPKIQNVSSSDLLMLLRQSPTP
HGLSLSDLQEAKYETFSDDPSPGAIDSNNSLSEMTHFRPQLHHSGDMVFT
PESGLQLRLNEKLGTTAATELKKLDFKVSSTSNNLISTIPSDNLAAGTDN
TSSLGPPSMPVHYDSQLDTTLFGKKSSPLTESGGPLSLSEENNDSKLLES
GLMNSQESSWGKNVSSTESGRLFKGKRAHGPALLTKDNALFKVSISLLKT
NKTSNNSATNRKTHIDGPSLLIENSPSVWQNILESDTEFKKVTPLIHDRM
LMDKNATALRLNHMSNKTTSSKNMEMVQQKKEGPIPPDAQNPDMSFFKML
FLPESARWIQRTHGKNSLNSGQGPSPKQLVSLGPEKSVEGQNFLSEKNKV
VVGKGEFTKDVGLKEMVFPSSRNLFLTNLDNLHENNTHNQEKKIQEEIEK
KETLIQENVVLPQIHTVTGTKNFMKNLFLLSTRQNVEGSYEGAYAPVLQD
FRSLNDSTNRTKKHTAHFSKKGEEENLEGLGNQTKQIVEKYACTTRISPN
TSQQNFVTQRSKRALKQFRLPLEETELEKRIIVDDTSTQWSKNMKHLTPS
TLTQIDYNEKEKGAITQSPLSDCLTRSHSIPQANRSPLPIAKVSSFPSIR
PIYLTRVLFQDNSSHLPAASYRKKDSGVQESSHFLQGAKKNNLSLAITLE
MTGDQREVGSLGTSATNSVTYKKVENTVLPKPDLPKTSGKVELLPKVHIY
QKDLFPTETSNGSPGHLDLVEGSLLQGTEGAIKWNEANRPGKVPFLRVAT
ESSAKTPSKLLDPLAWDNHYGTQIPKEEWKSQEKSPEKTAFKKKDTILSL
NACESNHAIAAINEGQNKPEIEVTWAKQGRTERLCSQNPPVLKRHQREIT
RTTLQSDQEEIDYDDTISVEMKKEDFDIYDEDENQSPRSFQKKTRHYFIA
AVERLWDYGMSSSPHVLRNRAQSGSVPQFKKVVFQEFTDGSFTQPLYRGE
LNEHLGLLGPYIRAEVEDNIMVTFRNQASRPYSFYSSLISYEEDQRQGAE
PRKNFVKPNETKTYFWKVQHHMAPTKDEFDCKAWAYFSDVDLEKDVHSGL
IGPLLVCHTNTLNPAHGRQVTVQEFALFFTIFDETKSWYFTENMERNCRA
PCNIQMEDPTFKENYRFHAINGYIMDTLPGLVMAQDQRIRWYLLSMGSNE
NIHSIHFSGHVFTVRKKEEYKMALYNLYPGVFETVEMLPSKAGIWRVECL
IGEHLHAGMSTLFLVYSNKCQTPLGMASGHIRDFQITASGQYGQWAPKLA
RLHYSGSINAWSTKEPFSWIKVDLLAPMIIHGIKTQGARQKFSSLYISQF
IIMYSLDGKKWQTYRGNSTGTLMVFFGNVDSSGIKHNIFNPPIIARYIRL
HPTHYSIRSTLRMELMGCDLNSCSMPLGMESKAISDAQITASSYFTNMFA
TWSPSKARLHLQGRSNAWRPQVNNPKEWLQVDFQKTMKVTGVTTQGVKSL
LTSMYVKEFLISSSQDGHQWTLFFQNGKVKVFQGNQDSFTPVVNSLDPPL
LTRYLRIHPQSWVHQIALRMEVLGCEAQDLY

Suitable calcium binding sites that are available for mutation in accordance with the present invention can be located within any one of the A1, A2, A3, C1, and/or C2 domains of the activated wild-type factor VIII. In a preferred embodiment, the calcium binding site is located in the A1 domain, particularly between residues 110-126 as identified (underlined) in SEQ ID NO: 2 above.

Exemplary recombinant factor VIII includes a point mutation involving a substitution of the glutamic acid residue at position 113 of SEQ ID NO: 2 (shown in bold typeface in SEQ ID NO: 2), with another residue that is other than aspartic acid. In particular, the substitutions at position 113 of SEQ ID NO: 2 can include, without limitation, the following substitutions: E113A, E113V, E113I, E113N, E113L, E113G, and E113M. Of these, the E113A substitution is preferred, having a specific activity that is at least about twice as great as wild-type factor VIII. The substitution at the E113 residue can also be made using the various modified forms and/or derivatives of the substituting amino acid residues noted above (see, e.g., Chem Files, Vol. 2, No. 4, "Unnatural Amino Acids II: The latest Update on New Tools for Drug Discovery" (available from Sigma-Aldrich), which is hereby incorporated by reference in its entirety). Thus, a preferred recombinant factor VIII according to the present invention includes an A1 domain that comprises one of the amino acid sequences of SEQ ID NO: 4-7, where the E113 residue has been mutated in accordance with the present invention.

Another property of the recombinant factor VIII of the present invention is its higher binding affinity for $Ca^{2+}$, $Mn^{2+}$, or possibly other cations as compared to that of the wild-type factor VIII.

Suitable mutant factor VIII sequences that can be modified in accordance with the present invention can also include any previously known or subsequently identified mutant factor VIII sequences that have modified properties with regard to various attributes, including, without limitation, antigenicity, circulating half-life, protein secretion, affinity for factor IXa and/or factor X, altered factor VIII-inactivation cleavage sites, stability of the activated factor VIII form, immunogenicity, and shelf-life.

One example of a suitable mutant factor VIII that can be modified in accordance with the present invention is a B-domainless factor VIII that contains amino acid residues 1-740 and 1690-2332 of SEQ ID NO: 2. (see, e.g., U.S. Pat. No. 6,458,563 to Lollar, which is hereby incorporated by reference in its entirety). Preferably, the recombinant B-domainless factor VIII contains one of the substitutions at position 113 identified herein.

In one embodiment of the B-domainless recombinant factor VIII of the present invention, the B-domain is replaced by a DNA linker segment and at least one codon is replaced with a codon encoding an amino acid residue that has the same charge as a corresponding residue of porcine factor VIII (see, e.g., U.S. Patent Application Publication No. 2004/0197875 to Hauser et al., which is hereby incorporated by reference in its entirety).

In another embodiment of the B-domainless recombinant factor VIII of the present invention, the modified mutant factor VIII is encoded by a nucleotide sequence having a truncated factor IX intron 1 inserted in one or more locations (see, e.g., U.S. Pat. No. 6,800,461 to Negrier and U.S. Pat. No. 6,780,614 to Negrier, which are hereby incorporated by reference in their entirety). This recombinant factor VIII can be used for yielding higher production of the recombinant factor VIII in vitro as well as in a transfer vector for gene therapy (see, e.g., U.S. Pat. No. 6,800,461 to Negrier, which is hereby incorporated by reference in its entirety). In a particular example of this embodiment, the recombinant factor VIII can be encoded by a nucleotide sequence having a truncated factor IX intron 1 inserted in two locations, and having a promoter that is suitable for driving expression in hematopoietic cell lines, and specifically in platelets (see, e.g., U.S. Pat. No. 6,780,614 to Negrier, which is hereby incorporated by reference in its entirety).

A second example of a suitable mutant factor VIII that can be modified in accordance with the present invention is a chimeric human/animal factor VIII that contains one or more animal amino acid residues as substitution(s) for human amino acid residues that are responsible for the antigenicity of human factor VIII. In particular, animal (e.g., porcine) residue substitutions can include, without limitation, one or more of the following: R484A, R488G, P485A, L486S, Y487L, Y487A, S488A, S488L, R489A, R489S, R490G, L491S, P492L, P492A, K493A, G494S, V495A, K496M, H497L, L498S, K499M, D500A, F501A, P502L, I503M, L504M, P505A, G506A, E507G, I508M, I508A, M2199I, F2200L, L2252F, V2223A, K2227E, and/or L2251_ (U.S. Pat. No. 5,859,204 to Lollar, U.S. Pat. No. 6,770,744 to Lollar, and U.S. Patent Application Publication No. 2003/0166536 to Lollar, each of which is hereby incorporated by reference in its entirety). Preferably, the recombinant chimeric factor VIII contains one of the substitutions at position 113 identified herein.

A third example of a suitable mutant factor VIII that can be modified in accordance with the present invention is a factor VIII that is characterized by greater stability of activated factor VIII by virtue of fused A2 and A3 domains. In particular, a factor VIII can be modified by substituting cysteine residues at positions 664 and 1826, resulting in a mutant factor VIII that includes a Cys664-Cys1826 disulfide bond that covalently links the A2 and A3 domains (Gale et al., "An Engineered Interdomain Disulfide Bond Stabilizes Human Blood Coagulation Factor VIIIa," *J. Thrombosis and Haemostasis* 1(9):1966-1971 (2003), which is hereby incorporated by reference in its entirety). Preferably, the recombinant fused domain (A2-A3) factor VIII contains one of the substitutions at position 113 identified herein.

A fourth example of a suitable mutant factor VIII that can be modified in accordance with the present invention is a factor VIII with altered inactivation cleavage sites (see, e.g., Amano et al., "Mutation at Either Arg336 or Arg562 in Factor VIII is Insufficient for Complete Resistance to Activated Protein C (APC)-Mediated Inactivation: implications for the APC Resistance Test," *Thrombosis & Haemostasis* 79(3): 557-63 (1998), which is hereby incorporated by reference in its entirety). These alterations can be used to decrease the mutant factor VIII's susceptibility to cleavage enzymes that normally inactivate the wild type factor VIII.

A fifth example of a suitable mutant factor VIII that can be modified in accordance with the present invention is a factor VIII that has enhanced affinity for factor IXa (see, e.g., Fay et al., "Factor VIIIa A2 Subunit Residues 558-565 Represent a Factor IXa Interactive Site," *J. Biol. Chem.* 269(32):20522-7 (1994); Bajaj et al., "Factor IXa: Factor VIIIa Interaction. Helix 330-338 of Factor IXa Interacts with Residues 558-565 and Spatially Adjacent Regions of the A2 Subunit of Factor VIIIa," *J. Biol. Chem.* 276(19):16302-9 (2001); and Lenting et al., "The Sequence Glu1811-Lys1818 of Human Blood Coagulation Factor VIII Comprises a Binding Site for Activated Factor IX," *J. Biol. Chem.* 271(4):1935-40 (1996), which are hereby incorporated by reference in their entirety) and/or factor X (see, e.g., Lapan et al., "Localization of a Factor X Interactive Site in the A1 Subunit of Factor VIIIa," *J. Biol. Chem.* 272:2082-88 (1997), which is hereby incorporated by reference in its entirety).

A sixth example of a suitable mutant factor VIII that can be modified in accordance with the present invention is a factor VIII that is modified to enhance secretion of the factor VIII (see, e.g., Swaroop et al., "Mutagenesis of a Potential Immunoglobulin-Binding Protein-Binding Site Enhances Secretion of Coagulation Factor VIII," *J. Biol. Chem.* 272(39): 24121-4 (1997), which is hereby incorporated by reference in its entirety).

A seventh example of a suitable mutant factor VIII that can be modified in accordance with the present invention is a factor VIII with an increased circulating half-life. This modification can be made using various approaches, including, without limitation, by reducing interactions with heparan sulfate (Sarafanov et al., "Cell Surface Heparan Sulfate Proteoglycans Participate in Factor VIII Catabolism Mediated by Low Density Lipoprotein Receptor-Related Protein," *J. Biol. Chem.* 276(15):11970-9 (2001), which is hereby incorporated by reference in its entirety) and/or low-density lipoprotein receptor-related protein ("LRP") (Saenko et al., "Role of the Low Density Lipoprotein-Related Protein Receptor in Mediation of Factor VIII Catabolism," *J. Biol. Chem.* 274 (53):37685-92 (1999); and Lenting et al., "The Light Chain of Factor VIII Comprises a Binding Site for Low Density Lipoprotein Receptor-Related Protein," *J. Biol. Chem.* 274(34): 23734-9 (1999), which are hereby incorporated by reference in their entirety).

An eighth example of a suitable mutant factor VIII that can be modified in accordance with the present invention is a modified factor VIII encoded by a nucleotide sequence modified to code for amino acids within known, existing epitopes to produce a recognition sequence for glycosylation at asparagines residues (see, e.g., U.S. Pat. No. 6,759,216 to Lollar, which is hereby incorporated by reference in its entirety). The mutant factor VIII of this example can be useful in providing a modified factor VIII that escapes detection by existing inhibitory antibodies (low antigenicity factor VIII) and which decreases the likelihood of developing inhibitory antibodies (low immunogenicity factor VIII). In one particular embodiment of this example, the modified factor VIII is mutated to have a consensus amino acid sequence for N-linked glycosylation. An example of such a consensus sequence is N-X-S/T, where N is asparagine, X is any amino acid, and S/T stands for serine or threonine (see U.S. Pat. No. 6,759,216 to Lollar, which is hereby incorporated by reference in its entirety).

A ninth example of a suitable mutant factor VIII that can be modified in accordance with the present invention is a modified factor VIII that is a procoagulant-active factor VIII having various mutations (see, e.g., U.S. Patent Application Publication No. 2004/0092442 to Kaufman et al., which is hereby incorporated by reference in its entirety). One example of this embodiment relates to a modified factor VIII that has been modified to (i) delete the von Willebrand factor binding site, (ii) add a mutation at Arg 740, and (iii) add an amino acid sequence spacer between the A2- and A3-domains, where the amino acid spacer is of a sufficient length so that upon activation, the procoagulant-active factor VIII protein becomes a heterodimer (see U.S. Patent Application Publication No. 2004/0092442 to Kaufman et al., which is hereby incorporated by reference in its entirety).

Further, the mutant factor VIII can be modified to take advantage of various advancements regarding recombinant coagulation factors generally (see, e.g., Saenko et al., "The Future of Recombinant Coagulation Factors," *J. Thrombosis and Haemostasis* 1:922-930 (2003), which is hereby incorporated by reference in its entirety).

The recombinant factor VIII of the present invention can be modified at position 113, as well as be modified to be B-domainless, to be chimeric, to have fused A2-A3 domains, to have altered inactivation cleavage sites, to have enhanced factor IXa and/or factor X affinity, to have enhanced secretion, to have an increased circulating half-life, to have mutant glycosylation sites, or to possess any two or more of such modifications in addition to the modification at position 113.

The recombinant factor VIII is preferably produced in a substantially pure form. In a particular embodiment, the substantially pure recombinant factor VIII is at least about 80% pure, more preferably at least 90% pure, most preferably at least 95% pure. A substantially pure recombinant factor VIII can be obtained by conventional techniques well known in the art. Typically, the substantially pure recombinant factor VIII is secreted into the growth medium of recombinant host cells. Alternatively, the substantially pure recombinant factor VIII is produced but not secreted into growth medium. In such cases, to isolate the substantially pure recombinant factor VIII, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the substantially pure recombinant factor VIII is subjected to gel filtration in an appropriately sized dextran or polyacrylamide column to separate the recombinant factor VIII. If necessary, a protein fraction (containing the substantially pure recombinant factor VIII) may be further purified by high performance liquid chromatography ("HPLC").

Another aspect of the present invention relates to an isolated nucleic acid molecule that encodes the recombinant factor VIII of the present invention. The isolated nucleic acid molecule encoding the recombinant factor VIII can be either RNA or DNA.

In one embodiment, the isolated nucleic acid molecule can have a nucleotide sequence encoding the amino acid sequence of SEQ ID NO: 2 as modified with one of the substitutions at position 113 (i.e., possessing one to three nucleotide substitutions within codon 113 of SEQ ID NO: 1 (nt 337-339)).

In another embodiment, the isolated nucleic acid molecule can have a nucleotide sequence encoding a B-domainless factor VIII of the type described above, as modified with one of the substitutions at position 113.

In another embodiment, the isolated nucleic acid molecule can have a nucleotide sequence encoding a chimeric human/porcine of the type described above, as modified with one of the substitutions at position 113.

In a further embodiment, the isolated nucleic acid molecule can have a nucleotide sequence encoding a fused A2-A3 domain factor VIII of the type described above, as modified with one of the substitutions at position 113.

In another embodiment, the isolated nucleic acid molecule can have a nucleotide sequence encoding a factor VIII whose inactivation sites have been modified as described above, as further modified with one of the substitutions at position 113.

In yet another embodiment, the isolated nucleic acid molecule can have a nucleotide sequence encoding a factor VIII whose affinity for factor IXa and/or factor X has been enhanced, as further modified with one of the substitutions at position 113.

In a still further embodiment, the isolated nucleic acid molecule can have a nucleotide sequence encoding a factor VIII whose affinity for various serum-binding proteins has been altered to increase its circulating half-life, as further modified with one of the substitutions at position 113.

In a further embodiment, the isolated nucleic acid molecule can have a nucleotide sequence encoding a factor VIII that has increased secretion in culture, as further modified with one of the substitutions at position 113.

In a further embodiment, the isolated nucleic acid molecule can have a nucleotide sequence encoding a factor VIII that possesses one or more non-naturally occurring glycosylation site, as further modified with one of the substitutions at position 113.

In yet another embodiment, the isolated nucleic acid molecule encodes a recombinant factor VIII that is modified at position 113 and is also modified to possess any two or more of the following: modified to be B-domainless, modified to be chimeric, modified to have fused A2-A3 domains, modified to have altered inactivation cleavage sites, modified to have enhanced factor IXa and/or factor X affinity, modified to have enhanced secretion, modified to have an increased circulating half-life, and modified to possess one or more non-naturally occurring glycosylation site.

Another aspect of the present invention relates to a recombinant DNA expression system that includes an isolated DNA molecule of the present invention, which expression system encodes a recombinant factor VIII. In one embodiment, the DNA molecule is in sense orientation relative to a promoter.

A further aspect of the present invention relates to a host cell including an isolated nucleic acid molecule encoding the recombinant factor VIII of the present invention. In a particular embodiment, the host cell can contain the isolated nucleic acid molecule in DNA molecule form, either as a stable plasmid or as a stable insertion or integration into the host cell genome. In another embodiment, the host cell can contain a DNA molecule in an expression system. Suitable host cells can be, without limitation, animal cells (e.g., baby hamster kidney ("BHK") cells), bacterial cells (e.g., *E. coli*), insect cells (e.g., Sf9 cells), fungal cells, yeast cells (e.g., *Saccharomyces* or *Schizosaccharomyces*), plant cells (e.g., *Arabidopsis* or tobacco cells), or algal cells.

The recombinant DNA expression system and host cells can be produced using various recombinant techniques well-known in the art, as further discussed below.

The DNA molecule encoding the recombinant factor VIII of the present invention can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements for the transcription and translation of the inserted protein-coding sequences. Thus, one embodiment of the present invention provides a DNA construct containing the isolated nucleic acid of the present invention, which is operably linked to both a 5' promoter and a 3' regulatory region (i.e., transcription terminator) capable of affording transcription and expression of the encoded recombinant factor VIII of the present invention in host cells or host organisms.

With respect to the recombinant expression system of the present invention, an expression vector containing a DNA molecule encoding the recombinant factor VIII of the present invention can be made using common techniques in the art. The nucleic acid molecules of the present invention can be inserted into any of the many available expression vectors using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. The selection of a vector will depend on the preferred transformation technique and target host for transformation.

A variety of host-vector systems may be utilized to express the recombinant factor VIII-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, etc.); insect cell systems infected with virus (e.g., baculovirus); and plant cells infected by bacteria (e.g., *Agrobacterium*). The expression elements of these vectors vary in their strength and specificities. Depending upon the host-vector system utilized, any one of a number of suitable transcription and translation elements can be used.

When recombinantly produced, the factor VIII protein or polypeptide (or fragment or variant thereof) is expressed in a recombinant host cell, typically, although not exclusively, a eukaryote.

Suitable vectors for practicing the present invention include, but are not limited to, the following viral vectors such as lambda vector system gt11, gtWES.tB, Charon 4, and plasmid vectors such as pCMV, pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993)), pQE, pIH821, pGEX, pET series (Studier et al, "Use of T7 RNA Polymerase to Direct Expression of Cloned Genes," *Methods in Enzymology* 185:60-89 (1990), which is hereby incorporated by reference in its entirety), and any derivatives thereof. Any appropriate vectors now known or later described for genetic transformation are suitable for use with the present invention.

Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Harbor, N.Y.: Cold Springs Laboratory, (1982), which is hereby incorporated by reference in its entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is generally desirable to use strong promoters in order to obtain a high level of transcription and, hence, expression of the gene. Depending upon the host cell system utilized, any one of a number of suitable promoters may be used. For instance, when cloning in *Escherichia coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

In one embodiment, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism.

An inducible promoter is a promoter that is capable of directly or indirectly activating transcription of one or more DNA sequences or genes in response to an inducer. In the absence of an inducer, the DNA sequences or genes will not be transcribed.

The DNA construct of the present invention can also include an operable 3' regulatory region, selected from among those which are capable of providing correct transcription termination and polyadenylation of mRNA for expression in the host cell of choice, operably linked to a DNA molecule which encodes for a protein of choice.

The vector of choice, promoter, and an appropriate 3' regulatory region can be ligated together to produce the DNA construct of the present invention using well known molecular cloning techniques as described in Sambrook et al., *Molecular Cloning: A Laboratory Manual*, Second Edition, Cold Spring Harbor Press, NY (1989), and Ausubel, F. M. et al. *Current Protocols in Molecular Biology*, New York, N.Y.: John Wiley & Sons (1989), which are hereby incorporated by reference in their entirety.

As noted, one alternative to the use of prokaryotic host cells is the use of eukaryotic host cells, such as mammalian cells, which can also be used to recombinantly produce the recombinant factor VIII of the present invention. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, and NS-1 cells.

Suitable expression vectors for directing expression in mammalian cells generally include a promoter, as well as other transcription and translation control sequences known in the art. Common promoters include SV40, MMTV, metallothionein-1, adenovirus Ela, CMV, immediate early, immunoglobulin heavy chain promoter and enhancer, and RSV-LTR.

Once the DNA construct of the present invention has been prepared, it is ready to be incorporated into a host cell. Accordingly, another aspect of the present invention relates to a method of making a recombinant cell. Basically, this method is carried out by transforming a host cell with a DNA construct of the present invention under conditions effective to yield transcription of the DNA molecule in the host cell. Recombinant molecules can be introduced into cells via transformation, particularly transduction, conjugation, mobilization, or electroporation.

In view of the recombinant technology discussed herein, another aspect of the present invention relates to a method of making a recombinant factor VIII of the present invention. This method involves growing a host cell of the present invention under conditions whereby the host cell expresses the recombinant factor VIII. The recombinant factor VIII is then isolated. In one embodiment, the host cell is grown in vitro in a growth medium. In a particular embodiment, suitable growth media can include, without limitation, a growth medium containing a von Willebrand Factor (referred to herein as "VWF"). In this embodiment, the host cell can contain a transgene encoding a VWF or the VWF can be introduced to the growth medium as a supplement. VWF in the growth medium will allow for greater expression levels of the recombinant factor VIII. Once the recombinant factor VIII is secreted into the growth medium, it can then be isolated from the growth medium using techniques well-known by those of ordinary skill in the relevant recombinant DNA and protein arts (including those described herein). In another embodiment, the method of making the recombinant factor VIII of the present invention further involves disrupting the host cell prior to isolation of the recombinant factor VIII. In this embodiment, the recombinant factor VIII is isolated from cellular debris.

When an expression vector is used for purposes of in vivo transformation to induce factor VIII expression in a target cell, promoters of varying strength can be employed depending on the degree of enhancement desired. One of skill in the art can readily select appropriate mammalian promoters based on their strength as a promoter. Alternatively, an inducible promoter can be employed for purposes of controlling when expression or suppression of factor VIII is desired. One of skill in the art can readily select appropriate inducible mammalian promoters from those known in the art. Finally, tissue specific mammalian promoters can be selected to restrict the efficacy of any gene transformation system to a particular tissue. Tissue specific promoters are known in the art and can be selected based upon the tissue or cell type to be treated.

Another aspect of the present invention relates to a method of making a recombinant factor VIII having increased specific activity compared to that of a wild-type factor VIII. This method involves altering the amino acid sequence of a wild-type factor VIII to yield a recombinant factor VIII. Alteration of the amino acid sequence of the wild-type factor VIII can include, for example, introducing at least one point mutation in or near at least one calcium binding site of the wild-type factor VIII. Thereafter, using protein analysis techniques well-known in the art, a determination can be made as to whether the recombinant factor VIII has increased specific activity compared to that of the wild-type factor VIII.

Another aspect of the present invention relates to a method of treating an animal for a blood disorder such as hemophilia, particularly hemophilia A. This method involves administering to an animal exhibiting hemophilia A an effective amount of the recombinant factor VIII of the present invention, whereby the animal exhibits effective blood clotting following vascular injury. A suitable effective amount of the recombinant factor VIII can include, without limitation, between about 10 to about 50 units/kg body weight of the animal. The animal can be any mammal, but preferably a human, a rat, a mouse, a guinea pig, a dog, a cat, a monkey, a chimpanzee, an orangutan, a cow, a horse, a sheep, a pig, a goat, or a rabbit.

The recombinant factor VIII of the present invention can be used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. In a particular embodiment, the recombinant factor VIII, alone, or in the form of a pharmaceutical composition (i.e., in combination with stabilizers, delivery vehicles, and/or carriers) is infused into patients intravenously according to the same procedure that is used for infusion of human or animal factor VIII.

Alternatively, or in addition thereto, the recombinant factor VIII can be administered by administering a viral vector such as an adeno-associated virus (Gnatenko et al., *Br. J. Haematol.* 104:27-36 (1999), which is hereby incorporated by reference in its entirety), or by transplanting cells genetically engineered to produce the recombinant factor VIII, typically via implantation of a device containing such cells. Such transplantation typically involves using recombinant dermal fibroblasts, a non-viral approach (Roth et al., *New Engl. J. Med.* 344:1735-1742 (2001), which is hereby incorporated by reference in its entirety).

The treatment dosages of recombinant factor VIII that should be administered to a patient in need of such treatment will vary depending on the severity of the factor VIII deficiency. Generally, dosage level is adjusted in frequency, duration, and units in keeping with the severity and duration of each patient's bleeding episode. Accordingly, the recombinant factor VIII is included in a pharmaceutically acceptable carrier, delivery vehicle, or stabilizer in an amount sufficient to deliver to a patient a therapeutically effective amount of the protein to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of recombinant factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher et al., *New Engl. J. Med.* 328:453-459 (1993); Pittman et al., *Blood* 79:389-397 (1992); and Brinkhous et al., *Proc. Natl. Acad. Sci.* 82:8752-8755 (1985), which are hereby incorporated by reference in their entirety.

Usually, the desired plasma factor VIII activity level to be achieved in the patient through administration of the recombinant factor VIII is in the range of 30-100% of normal. In one embodiment, administration of the therapeutic recombinant factor VIII is given intravenously at a preferred dosage in the range from about 5 to 50 units/kg body weight, and particularly in a range of 10-50 units/kg body weight, and further particularly at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453-1474, 1460, in *Hematology*, Williams, W. J., et al., ed. (1990), which is hereby incorporated by reference in its entirety. Patients with inhibitors may require a different amount of recombinant factor VIII than their previous form of factor VIII. For example, patients may require less recombinant factor VIII because of its higher specific activity than the wild-type VIII and its decreased antibody reactivity. As in treatment with human or plasma-derived factor VIII, the amount of therapeutic recombinant factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed recombinant factor VIII.

Treatment can take the form of a single intravenous administration of the recombinant factor VIII or periodic or continuous administration over an extended period of time, as required. Alternatively, therapeutic recombinant factor VIII can be administered subcutaneously or orally with liposomes in one or several doses at varying intervals of time.

The recombinant factor VIII can also be used to treat uncontrolled bleeding due to factor VIII deficiency in hemophiliacs who have developed antibodies to human factor VIII.

It has been demonstrated herein that the recombinant factor VIII of the present invention can differ in specific activity from the wild-type factor VIII. Factor VIII proteins having greater procoagulant activity from wild-type factor VIII are useful in treatment of hemophilia because lower dosages will be required to correct a patient's factor VIII deficiency. This will not only reduce medical expense for both the patient and the insurer, but also reduce the likelihood of developing an immune response to the factor VIII (because less antigen is administered).

EXAMPLES

Materials and Methods

Recombinant wild-type factor VIII (Kogenate™) was obtained from Bayer Corporation (Berkeley, Calif.). Phospholipid vesicles containing 20% phosphatidylserine (PS), 40% phosphatidylcholine (PC), and 40% phosphatidylethanolamine (PE) were prepared using octylglucoside as described previously (Mimms et al., Biochemistry 20:833-840 (1981), which is hereby incorporated by reference in its entirety). The reagents α-thrombin, factor IXaβ, factor X, and factor Xa (Enzyme Research Laboratories, South Bend, Ind.), hirudin, phospholipids, $MnCl_2$ (Sigma, St. Louis, Mo.), and the chromogenic Xa substrate S-2765 (N-α-benzyloxycarbonyl-D-arginyl-glycyl-L-arginyl-p-nitroanilide-dihydrochloride) (DiaPharma, West Chester, Ohio) were purchased from the indicated vendors. The B domainless factor VIII (FVII-IHSQ) expression construct HSQ-MSAB-NotI-RENeo was obtained from Dr. Pete Lollar and John Healey (see, e.g., Barrow et al., Blood 97:169-174 (2001), which is hereby incorporated by reference in its entirety).

Factor VIII LC, HC, A1, and A2 subunits were isolated from factor VIII as previously described (Fay et al., J. Biol. Chem. 276:12434-12439 (2001), which is hereby incorporated by reference in its entirety). Proteins were dialyzed into 10 mM MES, 0.3 M KCl, 0.01% Tween-20, pH 6.5, and stored at –80° C.

Example 1

Construction, Expression and Purification of B-Domainless Factor VIII Mutants B domainless-factor VIII cDNA was restricted from the factor VIII expression construct HSQ-MSAB-NotI-RENeo, using the endonucleases XhoI and NotI, and cloned into the Bluescript II K/S⁻ vector. Factor VIII molecules bearing single point mutation of Glu110Ala, Glu110Asp, Glu113Ala, Asp115Ala, Asp116Ala, Glu122Ala, Glu122Asp, Glu124Ala, Asp125Ala, or Asp126Ala, were constructed. Mutations were introduced into the shuttle constructs using the Stratagene QuickChange site-directed mutagenesis kit (Stratagene, La Jolla, Calif.) as described in Jenkins et al., Blood 100:501-508 (2002), which is hereby incorporated by reference in its entirety. Upon confirmation of the presence of only the desired mutations by dideoxy-sequencing, the appropriate fragment was restricted and cloned back into the factor VIII expression construct. Presence of only the desired mutations was confirmed by a second round of dideoxy-sequencing (Integrated DNA Technologies, Coralville, Iowa).

The factor VIII expression vector constructs were transfected in BHK cells using FuGene6 (Roche, Indianapolis, Ind.). The selection, sub-cloning, and cloning of stable transfectants were performed by standard methods and the cloned cells were cultured in roller bottles (Jenkins et al., Blood 100:501-508 (2002), which is hereby incorporated by reference in its entirety). The conditioned media was collected daily and the expressed proteins were purified using a one-step chromatography scheme as follows. The conditioned medium (~0.3 L) was centrifuged at 3,000×g for 20 min and the supernatant was filtered through 0.22 um filter. The pH of the filtrate was adjusted to 6.0 and material was loaded onto a column of SP-sepharose (5 ml; Amersham-Pharmacia) equilibrated with 10 mM MES, pH 6.0, 0.2 M NaCl, 0.01% Tween 20. After washing with 20 mM HEPES, pH 7.2, 0.2 M NaCl, 0.01% Tween 20, the bound factor VIII was eluted by with 20 mM HEPES, pH 7.2, 0.8 M NaCl, 0.01% Tween 20. Active fractions were detected using a one-stage clotting assay, pooled and dialyzed against 10 mM MES pH 6.5, 0.3 M KCl, 0.01% Tween 20 in Chelex100 treated $ddH_2O$. Resultant factor VIII forms were typically >80% pure as judged by SDS-polyacrylamide gel electrophoresis with albumin representing the major contaminant. Factor VIII samples were quick frozen and stored at –80° C.

Example 2

Factor Xa Generation Assays

The rate of conversion of factor X to factor Xa was monitored in a purified system (Lollar et al., Methods Enzymol. 222:128-143 (1993), which is hereby incorporated by reference in its entirety) according to the method previously described in Wakabayashi et al., Biochemistry 40:10293-10300 (2001); Wakabayashi et al., Biochemistry 41:8485-8492 (2002), which are hereby incorporated by reference in their entirety. Activity was determined as the amount of factor Xa generated (nM) per minute and converted to a value per nM factor VIII.

Example 3

Preincubation of Factor VIII Subunits with $Ca^{2+}$

Mixtures of A1 and A3-C1-C2 (2 μM and 1 μM, respectively, in 10 mM MES, 0.3 M KCl, 0.01% Tween-20, 0.01% BSA, pH 6.5) and A2 (10 μM in 20 mM HEPES, 0.05 M KCl, 0.01% Tween-20, 0.01% BSA, pH 7.2) were separately pre-incubated with 3 mM $Ca^{2+}$ or 0.1 mM EDTA for 18 hour at 4° C. Reactions were initiated by mixing A1/A3-C1-C2 and A2 solutions at a final subunit concentration of 40/20/200 nM (A1/A3-C1-C2/A2) in 20 mM HEPES, 0.05 M KCl, 0.01% Tween 20, 0.01% BSA, pH 7.2 (residual $Ca^{2+}$ and EDTA concentrations were 0.3 mM and 4 μM, respectively). At the indicated times, aliquots were removed and the activity was measured by the factor Xa generation assay.

Example 4

Isothermal Titration Calorimetry for $Ca^{2+}$ Binding on A1

Isothermal titration calorimetry (ITC) was performed to measure $Ca^{2+}$ binding to the isolated A1 subunit using a VP-ITC MicroCalorimetry Systems Instrument (MicroCal, Northampton, Mass.). The concentration of A1 was determined by $A_{280}$ value using an extinction coefficient=58,350 $cm^{-1}M^{-1}$ based upon the amino acid sequence for the A1 domain (factor VIII residues 1-372) according to the method of Gill and von Hippel (Gill et al., Anal. Biochem. 182:319-326 (1989), which is hereby incorporated by reference in its entirety). A1 subunit (25.6 μM) was treated with 10 mM EDTA for 18 hours at 4° C., followed by a dialysis against 10 mM MES, pH 6.5, 0.3 M KCl, 0.01% Tween20. The dialysis buffer was made using Chelex 100 treated $H_2O$ and the system was extensively washed with Chelex 100-treated $H_2O$ prior to use. Samples and buffers were degassed prior to analysis. The A1-containing solution was placed in a 1.44 ml sample cell. A 700 µL syringe loaded with 2 mM $CaCl_2$ in the same buffer was used for a series of automatic injections of 2 µL each into the A1 solution while mixing at a rate of 290 rpm at 30° C. The cumulative total of the heat evolved was plotted against the total $Ca^{2+}$ concentration to produce a binding isotherm. Each injection was followed by a 240 s pause to allow the system to return to a baseline value. Since heat produced from dilution, as measured by injecting the $Ca^{2+}$ solution into the sample cell containing only the buffer, was negligible, the uncorrected data was used for the analysis. An identical independent binding model was fit to the data and thermodynamic parameters [enthalpy ($\Delta H^0$), $K_d$, and molar binding stoichiometry (n)] were determined by nonlinear least squares regression using the ORIGIN software. Subsequently Gibbs free energy ($\Delta G$) and entropy ($\Delta S^0$) were calculated from the fitted values.

Example 5

Factor VIII Activity Titration Using $Ca^{2+}$- or $Mn^{2+}$-EGTA

EGTA buffer with free $Ca^{2+}$ concentrations of 0-6.5 mM and $Mn^{2+}$-EGTA buffer with free $Mn^{2+}$ concentrations of 0-0.75 mM in the presence of 2 mM EGTA were prepared as previously described (Wakabayashi et al., *Biochemistry* 41:8485-8492 (2002); Wakabayashi et al., *Biochemistry* 42:145-153 (2003), which are hereby incorporated by reference in their entirety). Wild type or mutant HSQ factor VIII (50 nM) was reacted in the $Ca^{2+}$-EGTA buffer or $Mn^{2+}$-EGTA buffer at 4° C. for 18 hours and resultant factor VIII activity was measured using the factor Xa generation assay. Non-linear least squares regression analysis was performed according to a single-site binding model using the formula, $$\text{Activity} = \frac{k \cdot [Me^{2+}]}{K_d + [Me^{2+}]} + C$$

where k is constant reflecting the metal ion induced activity, $[Me^{2+}]$ is either free $Ca^{2+}$ or free $Mn^{2+}$ concentration, $K_d$ is the dissociation constant, and C is constant reflecting the basal activity in the absence of exogenous metal ion.

Example 6

Enzyme-Linked Immunoadsorbant Assay

A sandwich ELISA was preformed to measure the concentration of HSQ factor VIII proteins (Jenkins et al., *Blood* 100:501-508 (2002), which is hereby incorporated by reference in its entirety). The procedure employed ESH8 (anti-factor VIII LC antibody; American Diagnostica) as a capture antibody and biotinylated R8B12 (anti-factor VIII A2 antibody; Green Mountain Antibodies) as the detection antibody. Thus, the epitopes for these antibodies are far-removed from the sites of mutagenesis. The amount of bound factor VIII was determined optically using a streptoavidin-linked horse radish peroxidase (Calbiochem) with the substrate O-phenylenenediamine dihydrochloride (Calbiochem) as previously described (Jenkins et al., *Blood* 100:501-508 (2002), which is hereby incorporated by reference in its entirety). Purified commercial recombinant factor VIII was used as the standard to determine the concentration of the samples. Factor VIII specific activity was determined from one-stage clotting assays and ELISA and is expressed as units/µg.

Example 7

Statistical Analysis

Nonlinear least-squares regression analysis was performed by Kaleidagraph (Synergy, Reading, Pa.) to obtain parameter values and standard deviations.

Example 8

Preincubation of Factor VIII Subunits with $Ca^{2+}$ or EDTA Followed by Activity Reconstitution It was previously demonstrated that maximal cofactor activity was achieved only when both HC and LC were pre-incubated with $Ca^{2+}$ (Wakabayashi et al., *Biochemistry* 41:8485-8492 (2002), which is hereby incorporated by reference in its entirety), suggesting that $Ca^{2+}$ binding to both HC and LC was necessary to generate active factor VIII. A similar evaluation of factor VIIIa reconstitution from the isolated A1, A2, and A3-C1-C2 was performed to determine the $Ca^{2+}$ requirement for the HC-derived A1 and A2 subunits in activity generation. The reconstitution of factor VIIIa is a two-step process with the initial association of A1 and A3-C1-C2 comprising the rate-limiting step and requiring several hours to complete (Regan et al., *J. Biol. Chem.* 270:8546-8552 (1995), which is hereby incorporated by reference in its entirety). Therefore, this first step was completed by mixing A1 and A3-C1-C2 subunits (2:1, mol:mol) in the presence of either 3 mM $Ca^{2+}$ or 0.1 mM EDTA for 18 hours. Activity generation was then monitored following the addition of A2 subunit, which, like the other subunits, was pre-incubated with either 3 mM $Ca^{2+}$ or 0.1 mM EDTA. The reconstituted A1/A3-C1-C2 dimer and A2 subunit were diluted 50-fold prior to reconstitution to prevent the EDTA-treated component from acquiring $Ca^{2+}$ at the time of reconstitution. Furthermore, the reconstitution time course (30 min) was short enough so that the dissociation of $Ca^{2+}$ from subunits upon their dilution was not a concern. Evaluation of the negative control (both A1/A3-C1-C2 dimer and A2 subunit pre-treated with EDTA) did not generate any activity over the reconstitution time course (FIG. 1). On the other hand, recombining the $Ca^{2+}$-treated A1/A3-C1-C2 dimer and A2 subunit resulted in the rapid generation of factor VIIIa activity (FIG. 1) that reached a maximal level within 10 min. When $Ca^{2+}$-treated A1/A3-C1-C2 was associated with EDTA-treated A2, the generated activity was similar to the positive control (~90% activity at 10 min and ~80% activity at 30 min). Assuming the association rates for $Ca^{2+}$ binding on each subunit was similar, these data suggested that there was little if any contribution of $Ca^{2+}$ binding to A2 subunit for activity generation. Consistent with this result was the failure to reconstitute factor VIIIa activity with the $Ca^{2+}$-treated A2 plus EDTA-treated dimer. These results, taken together with the earlier observation on the requirement for $Ca^{2+}$-binding to HC for efficient factor VIII reconstitution (Wakabayashi et al., *Biochemistry* 41:8485-8492 (2002), which is hereby incorporated by reference in its entirety) indicates that $Ca^{2+}$ binding to A1 subunit is a prerequisite for activity generation.

Example 9

Ca²⁺ Binding to A1 Detected by ITC

Figure 2:
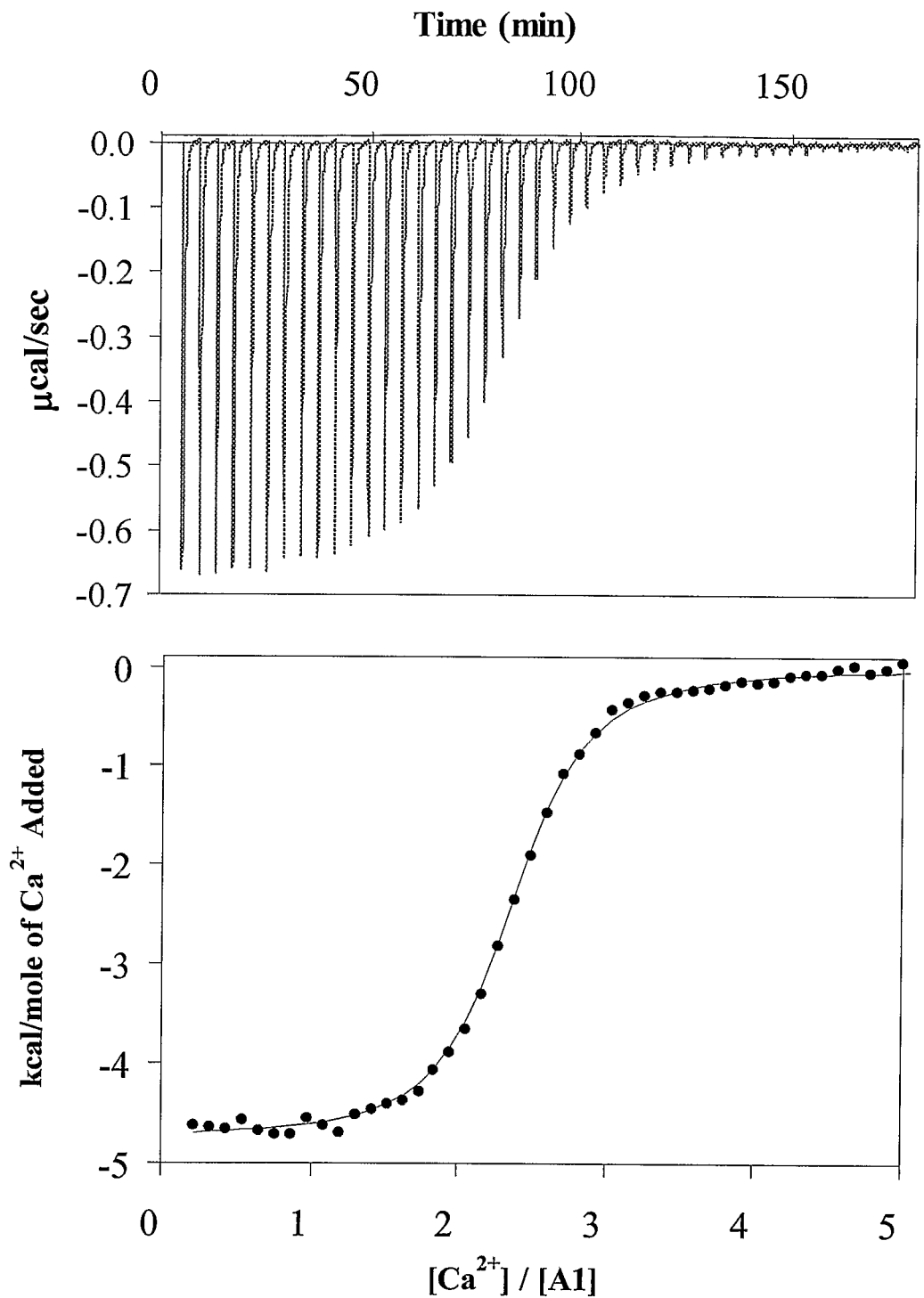
FIG. 2 shows the isothermal titration calorimetry of $Ca^{2+}$ binding to the A1 subunit at 30° C. The top panel shows the heat signal for 30 injections of 2 μL aliquots of 2 mM $Ca^{2+}$ into a 1.44 ml cell containing 25.6 μM A1. Both $Ca^{2+}$ and A1 were in 10 mM MES, pH 6.5, 0.3 M KCl, 0.01% Tween 20. The bottom panel shows the integrated heat for each injection after normalization to the amount of $Ca^{2+}$ added. Lines were drawn from the curve fit using Origin software. The apparent thermodynamic parameters describing the fit are n=2.40±0.01, $K_d$=0.74±0.05 μM, and $\Delta H^0$=−4.76±0.03 kcal/mol. $\Delta S^0$ was subsequently calculated as 12.3 cal/mol/K.

The binding of $Ca^{2+}$ to isolated A1 subunit was directly examined using ITC. Initial $Ca^{2+}$ injections into the A1-containing solution showed a large exothermic peak (FIG. 2), providing direct evidence for binding of the metal ion to the factor VIIIa subunit. Data were fitted using an identical independent binding model for cautious interpretation. The apparent thermodynamic values obtained from the binding isotherm were $\Delta H^{\circ}=-4.76\pm0.03$ kcal/mole and $K_d=0.74\pm0.05$ μM. $\Delta S^{\circ}$ and $\Delta G$ values were calculated as 12.3 kcal/mol/K and −8.5 kcal/mol, respectively. Thus, $\Delta H^{\circ}$ comprised 56% of $\Delta G$, indicating that there was nearly equal contribution of enthalpy and entropy to the free energy change following the binding of $Ca^{2+}$ to the A1 subunit. The observation of a large entropy change upon $Ca^{2+}$ binding to A1 suggested a complex mechanism likely involving a significant conformational component. Interestingly, a stoichiometry of 2.4 was obtained from the fitted data indicating the presence of more than one $Ca^{2+}$ sites contained within the A1 subunit.

Example 10

Factor VIII Mutations of a Putative Ca²⁺-Binding Site in A1

The data presented in Examples 8 and 9 indicate the presence of a $Ca^{2+}$ site(s) within the A1 domain of factor VIII that is (are) required for cofactor activity. Based upon the homology of factor VIII residues 110-126 to the residues comprising a putative $Ca^{2+}$-binding site localized in factor V, a series of point mutations were constructed where acidic residues were replaced with Ala (or in some cases Asp). The stable transfectants were expressed as B-domainless factor VIII in BHK cells and recombinant factor VIII was purified as described in Example 1 (supra). The freshly purified factor VIII preparations (mutants and wild type) were dialyzed against metal ion-free buffer, and specific activity values were determined by one-stage clotting and sandwich ELISA assays (Table 1).

TABLE 1

Specific Activity of Factor VIII Wild Type and Mutant Forms

| | Specific Activity | |
|---|---|---|
| Wild Type | 4.77 ± 0.54[a] | (100.0[b]) |
| E110A | 0.18 ± 0.03 | (3.8) |
| E110D | 0.48 ± 0.09 | (10.1) |
| E113A | 9.78 ± 0.03 | (205.0) |
| D115A | 5.04 ± 0.49 | (105.5) |
| D116A | 0.54 ± 0.02 | (11.3) |
| E122A | 0.58 ± 0.01 | (12.2) |
| E122D | 1.07 ± 0.24 | (22.4) |
| E124A | 2.11 ± 0.10 | (44.3) |
| D125A | 0.46 ± 0.01 | (9.6) |
| D126A | 0.59 ± 0.13 | (12.5) |

The activity and the concentration of each factor VIII preparation was measured by a one stage clotting assay and by ELISA, respectively, as described herein, and specific activity was calculated.
[a]Unit/μg
[b]Relative activity (% of wild type)

This treatment resulted in the retention of a significant level of activity, as judged by a specific activity of 4.8 units/μg for the wild type factor VIII, while removing exogenous metal ions from the protein preparations. The activity observed under these conditions likely reflected retention of a metal ion(s), possibly $Ca^{2+}$, which is (are) not readily released in the absence of chelators. This property is not due to the presence of single chain factor VIII (~30-50% of total factor VIII) in the recombinant preparations since partial purification of the factor VIII to enrich for single chain material yielded a similar specific activity as the unfractionated factor VIII preparation.

Several of the Ala-substituted point mutations (E110A, D116A, E122A, D125A, and D126A) exhibited marked reductions in specific activity to levels of ~4 to 12% of the wild type value (Table 1 (supra)). Thus the reduction in volume of the side chain and/or loss in electrostatic potential may result in slight conformational changes within this region that impair cofactor activity. Since results from a prior study evaluating a $Ca^{2+}$ site in lactalbumin showed the importance of side chains when replacing critical residues (Anderson et al., *Biochemistry* 36:11648-11654 (1997), which is hereby incorporated by reference in its entirety), selected, additional mutants were made with the conservative substitution of Asp for Glu at residues 110 and 122. As shown in Table I (supra), significantly greater activity was retained in the E110D and E122D mutants (10.1 and 22.4%, respectively) compared with E110A and E122A mutants (3.8 and 12.2%, respectively).

Example 11

Cofactor Activity Generated from Factor VIII Mutants Following Titration with Ca²⁺

Prior studies examining $Ca^{2+}$ binding in factor VIII employed isolated HC and LC prepared from the EDTA-treated heterodimer (Wakabayashi et al., *Biochemistry* 40:10293-10300 (2001); Wakabayashi et al., *Biochemistry* 41:8485-8492 (2002), which are hereby incorporated by reference in their entirety). Mixing of chains in the absence of $Ca^{2+}$ resulted in no regenerated activity. As shown herein, limitations in the amounts of mutant factor VIII precluded chain separation and purification. However, it was observed that the basal activity of the factor VIII measured in the absence of exogenous metal could be increased ~2-3-fold with saturating levels of $Ca^{2+}$. This incremental activity increase provided a functional assay for the binding of $Ca^{2+}$ to the factor VIII A1 domain mutants.

Figure 3A:
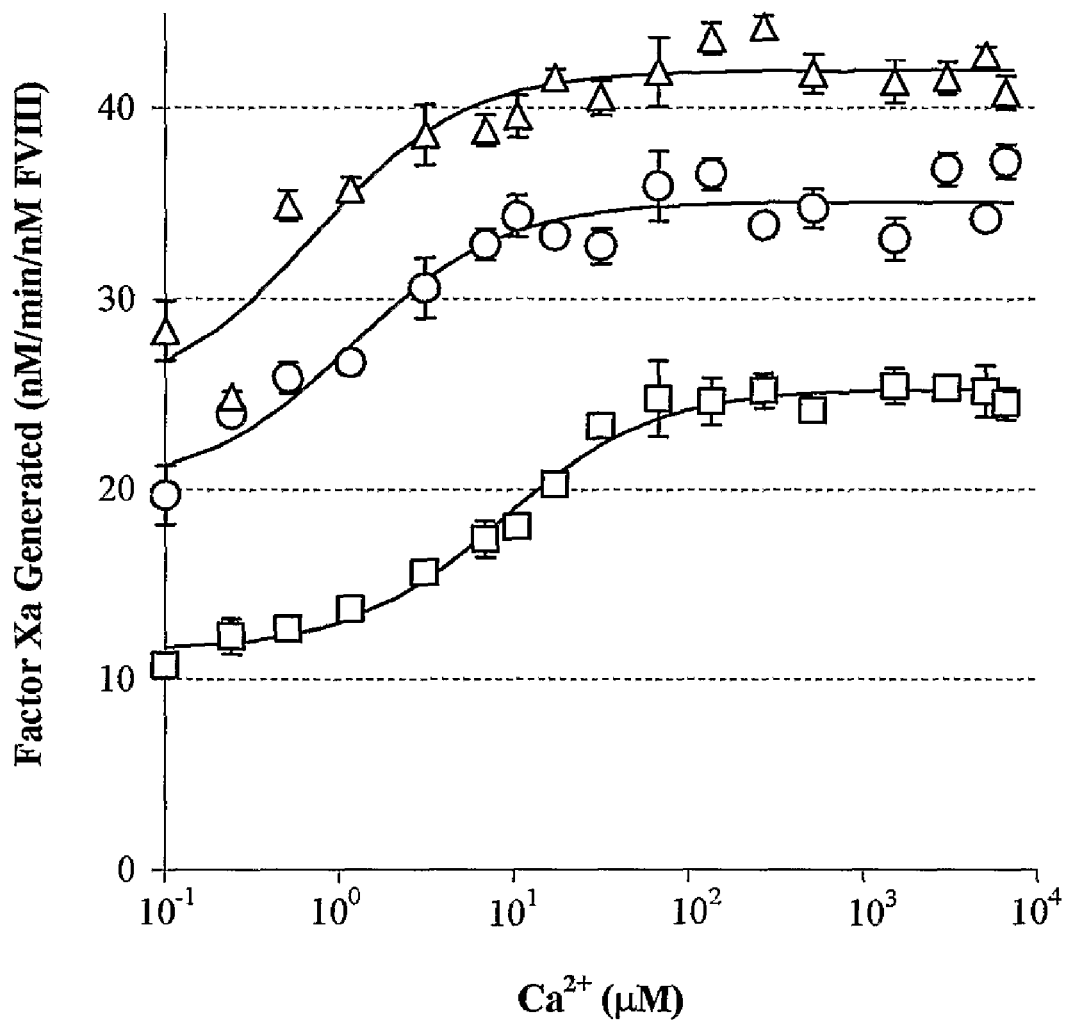
FIGS. 3A-3C are graphs showing factor VIII activity following titration with $Ca^{2+}$. B-domainless-factor VIII forms (50 nM) in the presence of the indicated amounts of free $Ca^{2+}$ with 2 mM EGTA were incubated for 18 hours at 4° C. and the factor VIII activity measured by a factor Xa generation assay as described in Example 2 (infra). Each point represents the average of four determinations.
Figure 3B:
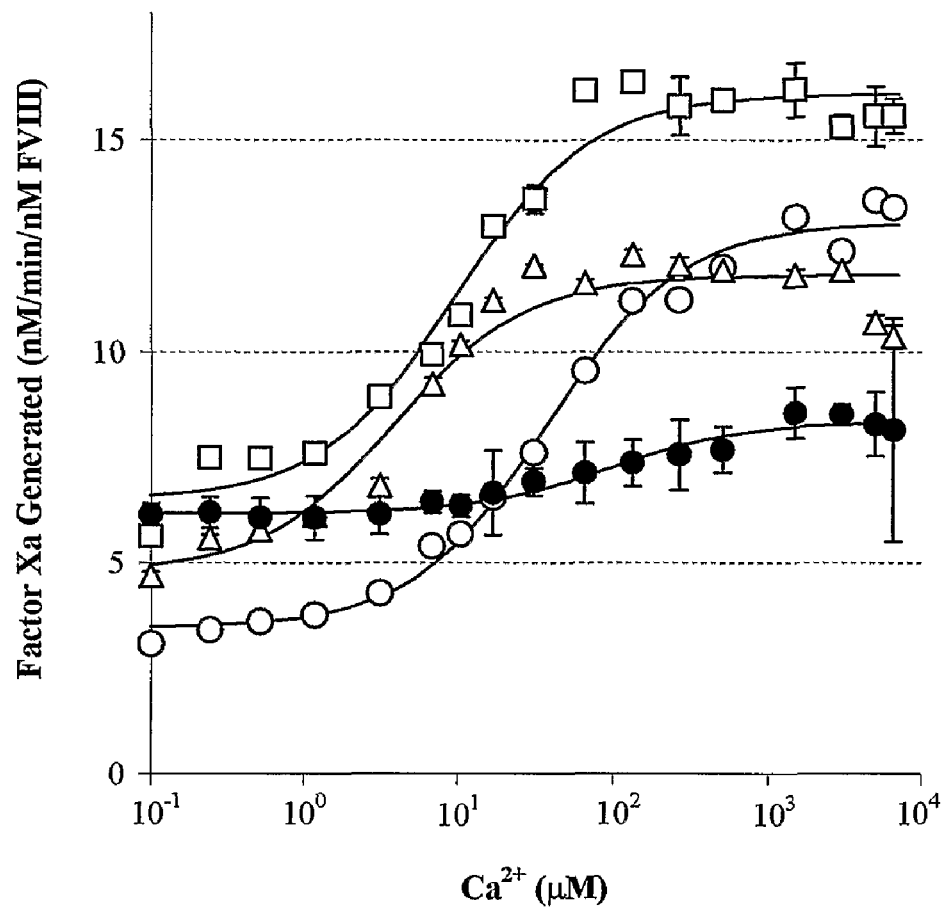
Figure 3C:
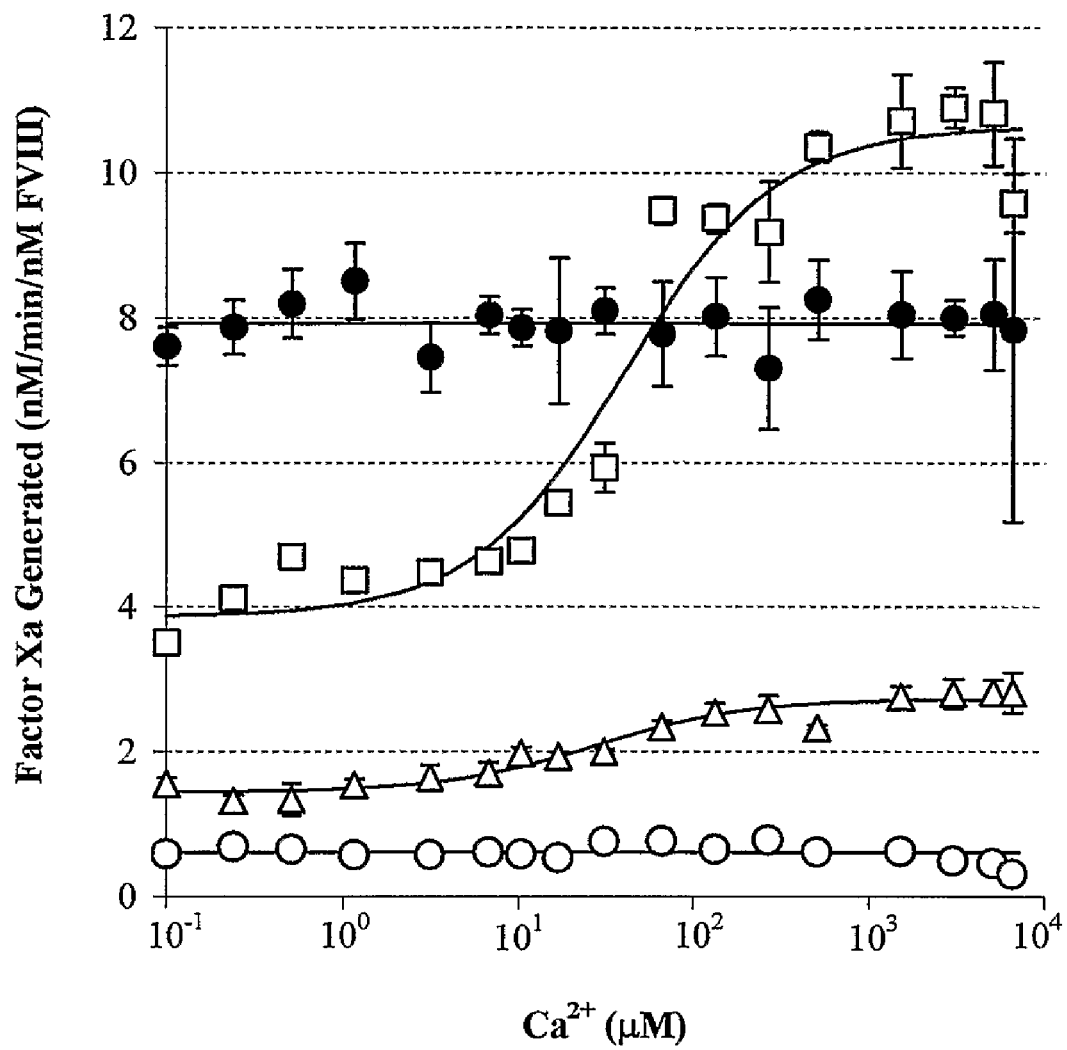

Increases in cofactor activity for the factor VIII wild type and 110-126 mutants in the absence of exogenous metal ion was determined following titration with $Ca^{2+}$. Results are presented in FIG. 3 and are arbitrarily divided into high (FIG. 3A), moderate (FIG. 3B) and low (FIG. 3C) activity factor VIII forms. Estimated parameter values determined by non-linear least-squares curve fitting are listed in Table 2 (infra). An optimized range of $Ca^{2+}$ concentrations (0-6.5 mM) was selected to cover the complete change in activity for all factor VIII forms. No significant increase in activity at higher concentrations of $Ca^{2+}$ (>10 mM) was observed. The k value indicates the difference between maximum activity at saturation with $Ca^{2+}$ and minimum activity with no exogenous metal ion present (C value). Therefore, the k value was used as an indicator to assess the activity response for each mutant to added $Ca^{2+}$.

Wild type factor VIII and many factor VIII mutants displayed an increase in activity in response to increases in the concentration of $Ca^{2+}$. Maximal activity response for the wild type reflected a high affinity for $Ca^{2+}$ ($K_d=1.18$ μM, Table 2-1) and this value compared favorably with a $K_d=8.9$ μM for $Ca^{2+}$ binding as measured in a functional assay for reconstituted factor VIII HC and LC (Wakabayashi et al., *Biochemistry* 41:8485-8492 (2002), which is hereby incorporated by reference in its entirety), as well as with the value determined above from ITC analysis of the isolated A1 subunit.

TABLE 2

Metal Ion Binding Parameters for Factor VIII Wild Type and Mutants

| | $Ca^{2+}$ Binding Parameters | | | $Mn^{2+}$ Binding Parameters | | | $C^c$(% of wild type) | |
|---|---|---|---|---|---|---|---|---|
| | $K_d$ (μM) | k | | $K_d$ (μM) | k | | | k |
| Wild Type | 1.18 ± 0.32 | 15.03 ± 1.09$^a$ | (100.0$^b$) | 1.40 ± 0.24 | 12.37 ± 0.46$^a$ | (100.0$^b$) | 20.08 ± 0.47$^a$ | (100.0$^b$) |
| E110A | n.d. | 0.00 ± 0.00 | (0.0) | 0.09 ± 0.03 | 1.23 ± 0.13 | (10.0) | 0.64 ± 0.25 | (3.2) |
| E110D | 27.79 ± 12.88 | 1.29 ± 0.13 | (8.6) | 0.48 ± 0.14 | 1.95 ± 0.15 | (15.8) | 1.45 ± 0.16 | (7.2) |
| E113A | 0.71 ± 0.24 | 17.43 ± 1.77 | (116.0) | 0.39 ± 0.09 | 15.97 ± 0.99 | (129.2) | 24.55 ± 1.12 | (122.3) |
| D115A | 8.44 ± 1.32 | 13.72 ± 0.51 | (91.3) | 0.61 ± 0.25 | 11.88 ± 1.32 | (96.0) | 11.56 ± 1.70 | (57.5) |
| D116A | 40.38 ± 7.46 | 6.78 ± 0.27 | (45.1) | 11.15 ± 2.25 | 3.33 ± 0.17 | (26.9) | 3.87 ± 0.23 | (19.3) |
| E122A | 37.43 ± 4.00 | 9.60 ± 0.22 | (63.9) | 4.11 ± 0.89 | 6.50 ± 0.33 | (52.5) | 3.46 ± 0.23 | (17.2) |
| E122D | 3.80 ± 1.04 | 7.06 ± 0.46 | (47.0) | 1.57 ± 0.37 | 6.65 ± 0.35 | (53.8) | 4.76 ± 0.32 | (23.7) |
| E124A | 9.51 ± 1.48 | 9.60 ± 0.35 | (63.9) | 0.32 ± 0.12 | 8.71 ± 0.96 | (70.5) | 6.50 ± 2.07 | (32.4) |
| D125A | n.d. | 0.00 ± 0.00 | (0.0) | n.d. | 0.00 ± 0.00 | (0.0) | 8.21 ± 0.35 | (40.9) |
| D126A | 97.62 ± 18.79 | 2.18 ± 0.09 | (14.5) | 0.29 ± 0.11 | 6.70 ± 0.75 | (54.1) | 6.17 ± 0.99 | (30.7) |

Figure 4A:
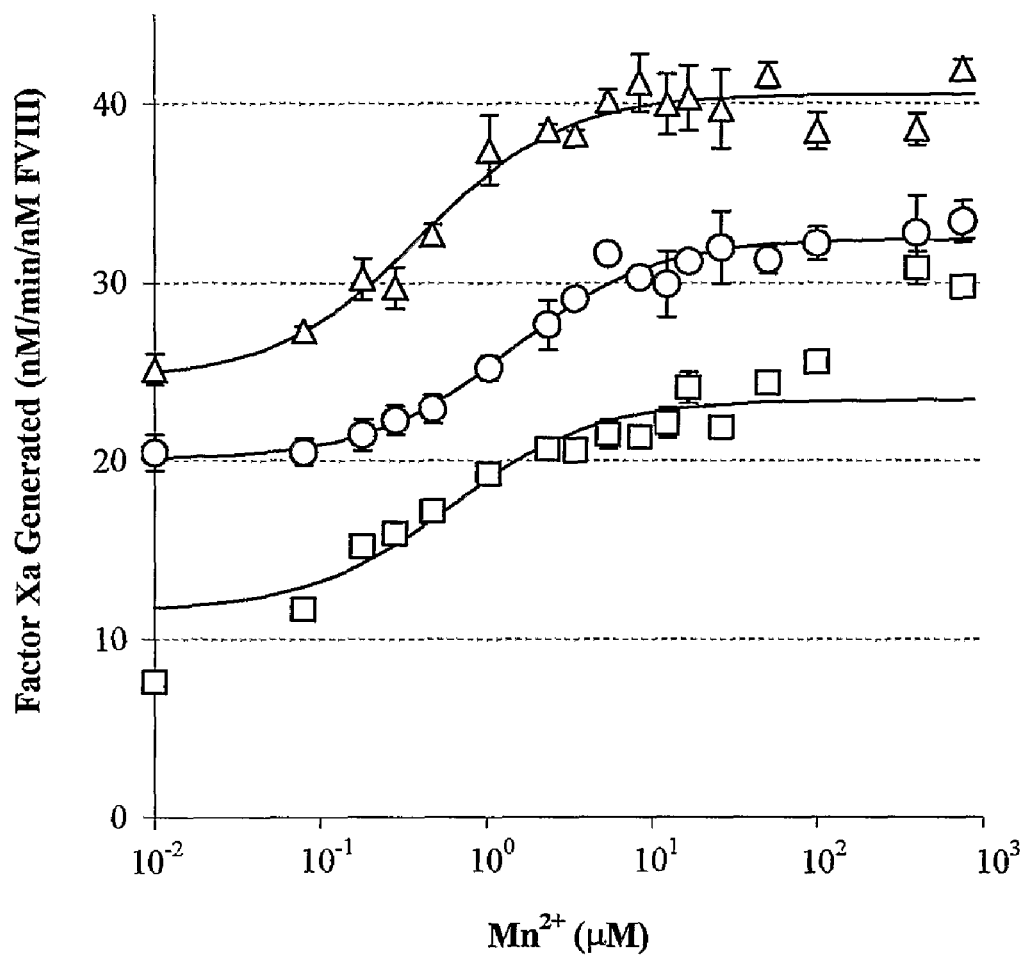
FIGS. 4A-4C are graphs showing factor VIII activity following titration with $Mn^{2+}$. B-domainless factor VIII forms (50 nM) in the presence of the indicated amounts of free $Mn^{2+}$ with 2 mM EGTA were assessed as described herein above with respect to FIGS. 3A-3C.
Figure 4B:
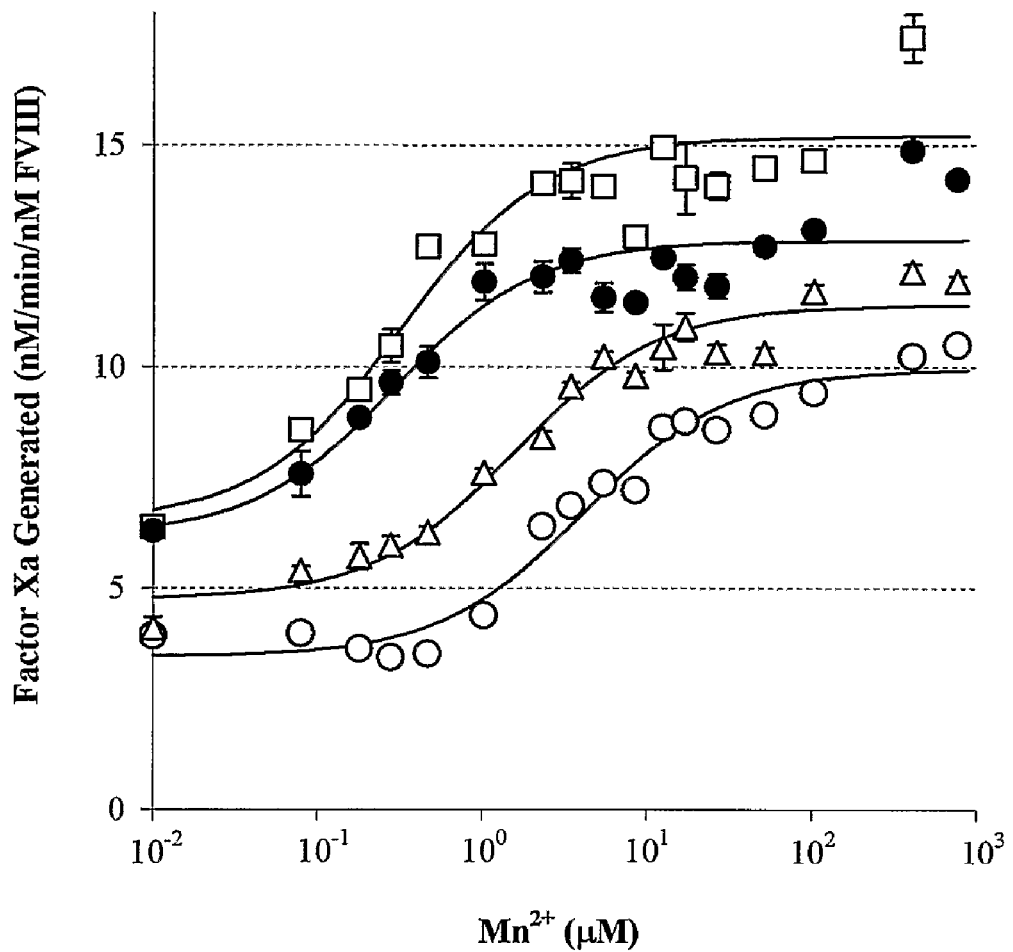
Figure 4C:
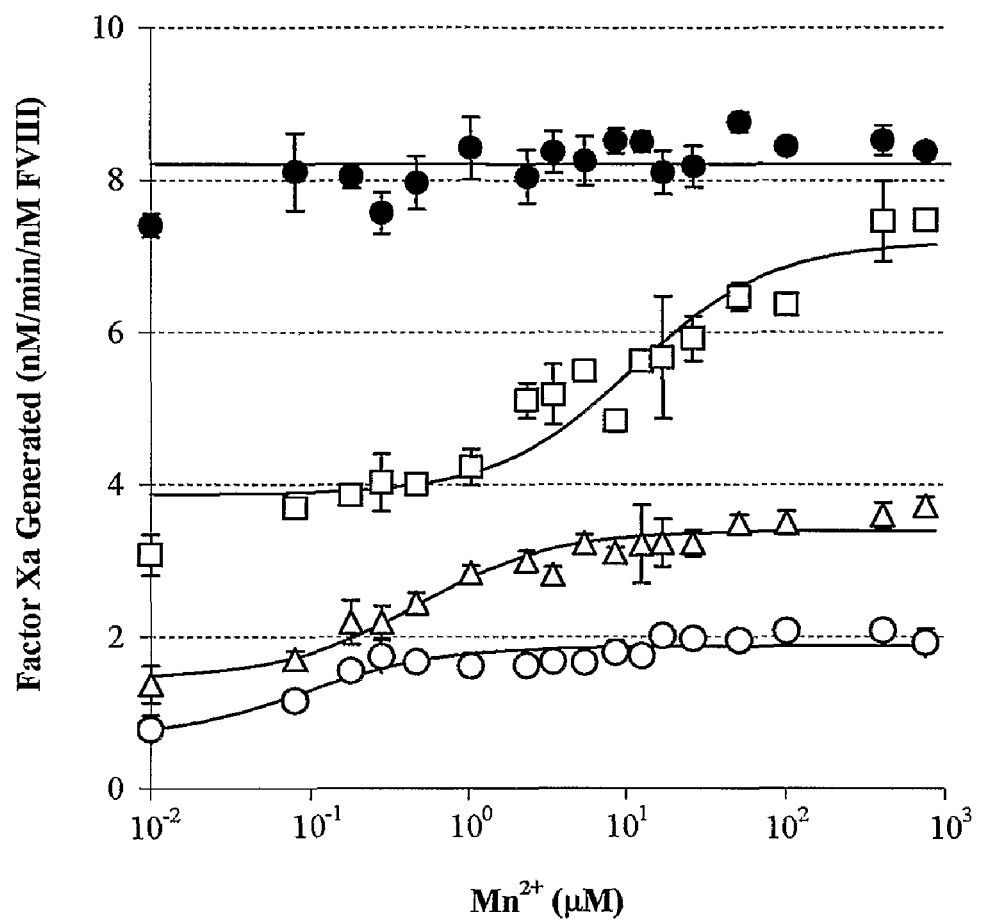

Parameter values (k, C, and $K_d$) were calculated by non-linear least-square regression from the data shown in FIGS. 3 and 4 using the formula shown herein.
n.d.; not determined.
$^a$Factor VIII activity is expressed as factor Xa generated (nM/min/nM factor VIII).
$^b$Relative activity (% of wild type)
$^c$C is the average of the estimated values obtained from FIGS. 3 and 4.

Two mutations (E113A and E122D) showed little deviation from the wild-type affinity parameters. On the other hand, four of the factor VIII mutants tested, E110D, D116A, E122A, and D126A showed ~25-90-fold increases in $K_d$ for $Ca^{2+}$ binding compared to wild type, indicating a marked reduction in affinity for the metal ion and suggesting a possible role for these residues in forming a $Ca^{2+}$ binding site. Comparison of the results obtained for E122D and E122A showing an ~3- and ~30-fold reduction in $Ca^{2+}$ affinity suggested the conserved substitution was relatively benign compared with the Ala substitution. A similar disparity was observed for mutation at E110 where the Asp substitution yielded an ~25-fold reduction in affinity while substitution with Ala appeared to eliminate the $Ca^{2+}$ binding site. These results suggested a significant role for these residues, especially E110, in $Ca^{2+}$ binding. The loss of $Ca^{2+}$ binding was also observed with mutation at D125. Based upon the observed defects in $Ca^{2+}$ binding and/or affinity, it was proposed that residues E110, D116, E122, D125 and D126 form a $Ca^{2+}$-coordination site in the A1 domain of factor VIII. It was also speculated that E110 and D125 are critical to this site since alteration of these residues appeared to result in loss of $Ca^{2+}$ binding. Furthermore, it was suggested that residues D115 and E124 make little contribution to $Ca^{2+}$ coordination. The basis for this contention is the minimal effect of Ala substitution on $Ca^{2+}$ binding at these sites, inasmuch as $K_d$ values were increased by <9-fold. This modest reduction in affinity may arise from Ala substitution at these residues affecting the contributions of the adjacent residues D116 and D125, respectively to the $Ca^{2+}$-binding site.

Example 12

Cofactor Activity Generated from Factor VIII Mutants Following Titration with $Mn^{2+}$ In a recent report, it was shown that $Mn^{2+}$ binds factor VIII with high affinity (5.7 μM) and results in similar stimulation of cofactor activity (Wakabayashi et al., *Biochemistry* 42:145-153 (2003), which is hereby incorporated by reference in its entirety). However, that study also revealed competition of $Tb^{3+}$ binding to factor VIII by $Mn^{2+}$ but not by $Ca^{2+}$, indicating that the $Mn^{2+}$ and $Ca^{2+}$ binding sites in factor VIII were not identical. In order to determine whether any of the residues we identify above as participating in binding $Ca^{2+}$ contribute to forming a $Mn^{2+}$-binding site, a similar approach was employed where factor VIII activity was measured in response to titration with $Mn^{2+}$. Results of these studies are shown in FIG. 4 and Table 2-2, and employed a range of $Mn^{2+}$ concentrations from 0-0.75 mM (concentrations >5 mM resulted in no further increase in activity). Several parallels in the response to $Ca^{2+}$ were observed using $Mn^{2+}$. Wild type factor VIII displayed a high affinity for $Mn^{2+}$ ($K_d$=1.40 μM). Most of the mutants showed an increase in activity following addition of $Mn^{2+}$, and activity values at saturating concentration of $Mn^{2+}$ (k values) were very similar to those observed for $Ca^{2+}$. Thus the value for the activity response varied depending upon the particular mutation rather than the metal ion used to saturate the response, suggesting that the activity response could result from modest changes in conformation that were unrelated to the specific metal-ion binding event. Therefore, with respect to this particular site in the A1 domain, both $Ca^{2+}$ and $Mn^{2+}$ generate activity by a mechanism affecting a common region crucial for cofactor function.

In contrast, while markedly reduced $Ca^{2+}$ affinities were observed for E122A and D126A, the affinity of these factor VIII mutations for $Mn^{2+}$ was either only marginally (~2-fold) reduced or unchanged, respectively. An ~8-fold reduction in $Mn^{2+}$ was observed for the mutant D116A (compared with a ~40-fold reduction in $Ca^{2+}$ affinity), and this result may suggest a role for D116 in the coordination of $Mn^{2+}$. Interestingly, the two mutations that showed little if any response to $Ca^{2+}$ (E110A and D125A) were also unresponsive to $Mn^{2+}$. Substitution of Asp for Glu at residue 110 partially restored $Ca^{2+}$-dependent function but had little effect on the $Mn^{2+}$-dependent activity, suggesting that this residue does not likely function in binding $Mn^{2+}$. While mutations at E110 showed marginal activity relative to wild type in the absence of exogenous metal ion (C=3.2% and 7.2% for Ala and Asp substitutions), the mutation D125A retained significant activity (C=41%). This observation indicated that mutation at D125 did not likely result in any global change in conformation that would diminish factor VIII activity. This observation adds strong support to the conclusion that D125 participates in the coordination of either $Ca^{2+}$ or $Mn^{2+}$.

Discussion of Examples 1-12

Previously, it was found that $Ca^{2+}$ (or $Mn^{2+}$) binding to factor VIII HC was essential for cofactor activity (Wakabayashi et al., *Biochemistry* 41:8485-8492 (2002); Wakabayashi et al., *Biochemistry* 42:145-153 (2003), which are hereby incorporated by reference in their entirety). A $Ca^{2+}$-binding site in the A1 domain of factor VIII has now been identified and tentatively localized. The occupancy of this binding site yields an increase in specific activity. Furthermore, the observation that $Ca^{2+}$ binding to A2 domain in HC contributes little if at all to generate cofactor activity highlights the functional role of the $Ca^{2+}$ binding site in A1 domain in HC. Recently, Zeibdawi et al. (Zeibdawi et al., *J. Biol. Chem.* 276:19929-19936 (2001), which is hereby incorporated by reference in its entirety) reported that residues 94-110 in factor V comprise a $Ca^{2+}$ binding site required for its activity. In the present application, the homologous region in the A1 domain of factor VIII (residues 110-126) for $Ca^{2+}$ binding was probed using a site-directed mutagenesis approach. Results show that mutation at each of several acidic amino acids (E110, D116, E122, D125, and D126) caused a marked reduction (or complete loss) of $Ca^{2+}$ binding affinity, providing evidence that these residues participate in coordinating $Ca^{2+}$. In addition, data from a complementary study revealed that in the absence of $Ca^{2+}$, D125 (and possibly D116) likely contribute to the coordination of $Mn^{2+}$. Thus, these results are consistent with an earlier report showing that $Ca^{2+}$ and $Mn^{2+}$ bind to non-identical sites in HC (Wakabayashi et al., *Biochemistry* 42:145-153 (2003), which is hereby incorporated by reference in its entirety) and further suggest that these sites are in close proximity to one-another.

Mechanism(s) by which $Ca^{2+}$ (or $Mn^{2+}$) generate active factor VIII remain largely unknown. The factor VIII A domain homology model (Pemberton et al., *Blood* 89:2413-2421 (1997), which is hereby incorporated by reference in its entirety) predicts residues 102-116 not to possess a defined secondary structure while residues 120-125 form an α-helix with a short β strand segment (residues 117-119) connecting the two segments. Based upon the results presented herein, it has been proposed that $Ca^{2+}$ stabilizes this region by forming bonds with E110, D116, E122, D125, and/or D126. This coordination would provide appropriate energy to fix in space the elongated region defined by 110-116. Furthermore, it is of interest to note that in the 5-domainal factor VIII model (Stoilova-McPhie et al., *Blood* 99:1215-1223 (2002), which is hereby incorporated by reference in its entirety), this region juxtaposes the C1 domain. While A1 and A3 domains appear to associate with a relatively extended interface, the interface between A1 and C1 is small. Thus, it can be that stabilizing a segment in A1 near C1 may add structure to a "hinge" region separating the A and C domains.

The above hypothesis is reinforced by the results obtained with $Mn^{2+}$, which is typically coordinated by acidic residues and/or His residues (Bertini et al., *Handbook on Metalloproteins*, New York, N.Y.: Marcel Dekker, Inc. (2001), which is hereby incorporated by reference in its entirety). There are two His residues in C1 (H2082 and H2137) that are in close proximity to residues 110-126 in A1. It is proposed that these His residues contribute to $Mn^{2+}$ coordination with D125 (and possibly D116). The result of this coordination could also stabilize the interaction of A1 and C1 by bridging these regions. This explanation is compatible with the results showing that $Ca^{2+}$ and $Mn^{2+}$ bind different sites (Wakabayashi et al., *Biochemistry* 42:145-153 (2003), which is hereby incorporated by reference in its entirety) yet generate active factor VIII of similar specific activity. Furthermore, this hypothesis also offers an explanation for the increase in $Mn^{2+}$ affinity observed for several of the A1 mutants. Thus some mutations may have resulted in an altered spatial separation between D125 (and D116) and His residue(s) H2082 and/or H2137 in C1 and this alteration may be favorable for $Mn^{2+}$ coordination, yielding a higher affinity for the metal ion. This hypothesis is compatible with preliminary data suggesting that the effects of $Ca^{2+}$ and $Mn^{2+}$ on factor VIII activity generation are neither additive nor synergistic.

Overall, the stabilization that is proposed to result from metal ion binding near the A1-C1 junction may be necessary to provide proper orientation of factor VIIIa subunits within the factor Xase complex. Significant data indicate an extended interface between factor VIIIa and factor IXa, mediated by residues in A2 and A3 domains of the cofactor (Mertens et al., *Thromb. Haemost.* 82:209-217 (1999), which is hereby incorporated by reference in its entirety, for review). While residues in A3 appear to provide the majority of the binding energy for this interaction (Lenting et al., *J. Biol. Chem.* 269:7150-7155 (1994), which is hereby incorporated by reference in its entirety), critical contacts between A2 subunit and the protease domain of factor IXa are required for cofactor function (Bajaj et al., *J. Biol. Chem.* 276:16302-16309 (2001), which is hereby incorporated by reference in its entirety). The latter is borne-out by the direct stimulation of factor IXa by the isolated A2 subunit (Fay et al., *J. Biol. Chem.* 273:19049-19054 (1998), which is hereby incorporated by reference in its entirety). While A1 subunit does not appear to contact factor IXa directly, inclusion of isolated A1 subunit results in a marked enhancement of the activity attributed to the isolated A2 subunit (Fay et al., *J. Biol. Chem.* 274:15401-15406 (1999), which is hereby incorporated by reference in its entirety). Thus A1 appears to function to orient A2 relative to the factor IXa protease domain. This property is further illustrated by truncation of A1 at R336 resulting in a dramatic loss in cofactor activity without significantly altering the inter-A1-A2 subunit affinity (Rosenblum et al., *J. Biol. Chem.* 277:11664-11669 (2002), which is hereby incorporated by reference in its entirety).

Factor VIII HC and LC associate in the absence of metal ion with moderate affinity ($K_d$=53.8±14.2 nM) (Wakabayashi et al., *Biochemistry* 40:10293-10300 (2001), which is hereby incorporated by reference in its entirety) and inclusion of either $Ca^{2+}$ or $Mn^{2+}$ did not change the affinity of this interaction ($K_d$=48.7±15.4 (Wakabayashi et al., *Biochemistry* 41:8485-8492 (2002), which is hereby incorporated by reference in its entirety) and 53.0±17.1 nM (Wakabayashi et al., *Biochemistry* 42:145-153 (2003), which is hereby incorporated by reference in its entirety) in the presence of $Ca^{2+}$ and $Mn^{2+}$, respectively). Thus the binding energy for interaction of HC and LC is likely derived from electrostatic and hydrophobic interactions between A1 and A3 domains. As described herein (supra), $Ca^{2+}$ or $Mn^{2+}$ binding the A1-C1 boundary region may create a fractional contribution to the total binding energy between HC and LC and thus remain undetected in the inter-chain affinity determination. Analysis of the kinetics of factor VIII activity generation of the HC/LC complex, associated in the absence of metal ions, following addition of $Ca^{2+}$ yielded a series reaction pattern, suggesting that $Ca^{2+}$ binding triggers certain conformational change(s) within the heterodimer to yield active factor VIII (Wakabayashi et al., *Biochemistry* 41:8485-8492 (2002), which is hereby incorporated by reference in its entirety). Conformational events suggested by the data presented herein may reflect the stabilization of the A1 110-126 region, followed by formation of a stable interface between this region and the region around H2137 in the C1 domain.

The presence of at least two $Ca^{2+}$ sites have been identified in isolated A1 subunit by ITC following its treatment with EDTA. The large entropy change observed upon binding $Ca^{2+}$ was consistent with a significant change in conformation of this domain as suggested herein (supra). The affinity value measured for the sites (~0.7 µM) was similar to the value that was obtained monitoring the increase in specific activity (1.18 µM for B-domain less wild type factor VIII). Furthermore, the fractional stoichiometry observed for occupancy of the isolated domain may suggest a dimerization of the subunit that is not observed with the intact heterodimer. The relationship of $Ca^{2+}$ sites in the A1 domain with other sites in factor VIII has not yet been established. While passive removal was observed of a putative $Ca^{2+}$ molecule(s) from the site proposed within residues 110-126, other metal ions likely remain associated as judged by the relatively high specific activity of the protein in solutions free from exogenous metal ions. Based upon the observation that pre-treatment of EDTA-treated factor VIII LC with $Ca^{2+}$ was required to obtain reconstitution of functional factor VIII (Wakabayashi et al., *Biochemistry* 41:8485-8492 (2002), which is hereby incorporated by reference in its entirety), it is speculated that $Ca^{2+}$ contained within sites in the LC may be retained in the absence of chelation. In support of this contention, preliminary data by ITC suggests the presence of multiple $Ca^{2+}$ sites in the factor VIII LC.

Several drawbacks to a loss-of-function mutagenesis approach in the localization of $Ca^{2+}$-binding sites have been noted. These include mutation to an Ala eliminating total $Ca^{2+}$ binding (Anderson et al., *Biochemistry* 36:11648-11654 (1997), which is hereby incorporated by reference in its entirety), or the elimination of charged residues far removed from a $Ca^{2+}$-binding site (Trigo-Gonzalez et al., *Biochemistry* 32:9826-9831 (1993); Ababou et al., *Biochemistry* 40:12719-12726 (2001), which are hereby incorporated by reference in their entirety) that result in reduced $Ca^{2+}$ affinity. However, the results presented herein are further supported by a recent, similar approach applied to the $Ca^{2+}$-binding site in factor V. The region comprised of residues 110-126 in factor VIII is highly homologous to residues 96-112 in factor V (FIG. 5). Recent data generated following site-directed mutagenesis within this region indicates that E96, D102, and D111 appear to be crucial residues for the association of factor Va HC and LC (Zeibdawi et al., *Biochem. J.* 377:141-148 (2003), which is hereby incorporated by reference in its entirety), an interaction that is $Ca^{2+}$-dependent in factor Va (Krishnaswamy et al., *J. Biol. Chem.* 264:3160-3168 (1989), which is hereby incorporated by reference in its entirety). Results indicating a role for factor VIII residues E110, D116 and D126 in $Ca^{2+}$ binding correspond to factor V residues E96, D102, and D111, respectively. These residues are conserved in all species of factor V and factor VIII identified to date. In addition, no role for residues E113, D115, and E124 in $Ca^{2+}$ coordination has been shown, and these residues are not conserved in factor V. Thus the identification of selected, homologous residues as determined in two independent studies provides mutual support for the role of this region in contributing to $Ca^{2+}$-coordination sites in the protein cofactors.

Example 13

Clotting Activity Following Saturation Mutagenesis at E113 of the Wild-Type Human Factor VIII Factor VIII molecules bearing the indicated (see FIG. 7) single point mutations at residue 113 were constructed according to the method described below. The factor VIII expression vector constructs (HSQ-MSAB-NotI-RENeo) were transfected into confluent Cos-7 cells using FuGene6 (Roche, Indianapolis, Ind.). After 1 day, the medium was changed to AIM-V (Invitrogen) and cultured for an additional 2 days. Conditioned medium containing the expressed factor VIII was collected and factor VIII activity was measured using a one-stage clotting assay. Activity is presented relative to a transfected wild-type control representing a value of (1). Results from this analysis show that mutant E113A possesses significantly greater clotting activity than that observed for the wild-type protein. Furthermore, several other point mutations at this position, including E133L, E113I, E113V, E113N, E113G and E113M show similar or modestly greater clotting activity compared with wild-type.

Figure 8:
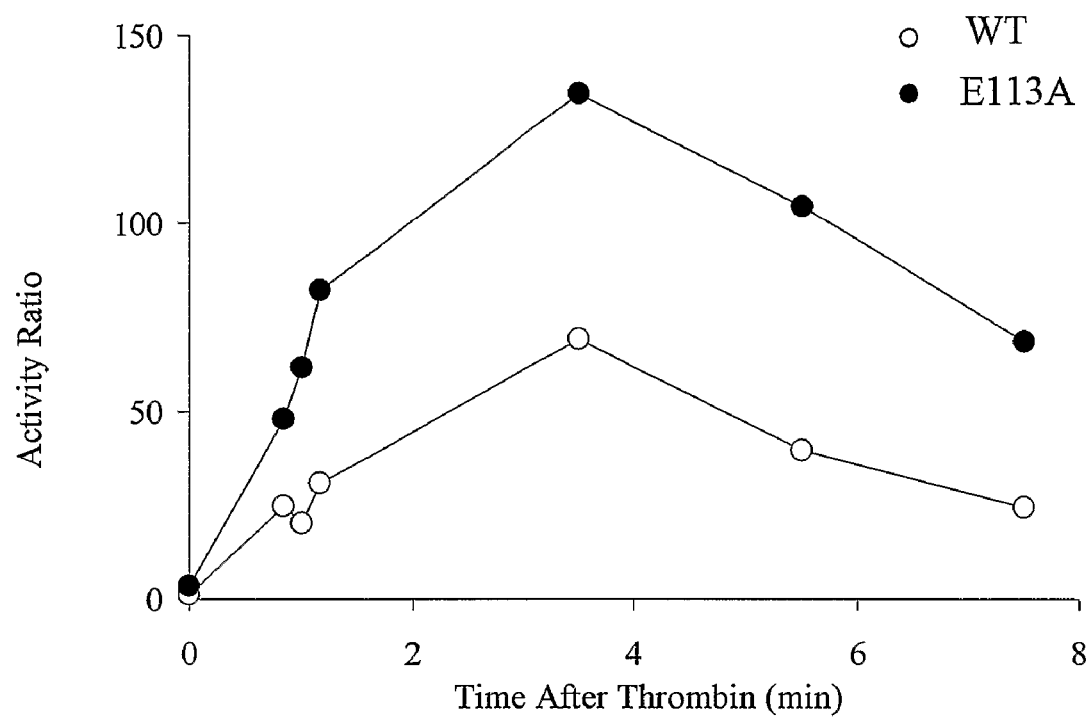
FIG. 8 is a graph showing factor VIII activity following activation by thrombin.

The clotting activity of the thrombin-activated factor VIII mutant E113A is shown in FIG. 8 below, which demonstrates that both factor VIII and factor VIIIa forms of the mutant demonstrate an ~2-fold increased activity.

Example 14

Experimental Methods for Determining that Factor VIII:E113A Represents a High Specific Activity Factor VIII Examples 1-12 above identify an acidic-rich segment in the A1 domain of factor VIII (residues 110-126) that functions in the coordination of $Ca^{2+}$, an ion necessary for cofactor activity (Wakabayashi et al., *J. Biol. Chem.* 279:12677-12684 (2004), which is hereby incorporated by reference in its entirety). Using Ala-scanning mutagenesis, it was determined that replacement of residue E113 with Ala yielded a factor VIII point mutant that possessed an ~2-fold increased affinity for $Ca^{2+}$ as compared with wild type, suggesting that this residue did not directly contribute to $Ca^{2+}$ coordination but rather modulated the affinity of the ion at this site. Furthermore, the E113A factor VIII possessed twice the specific activity of wild type as determined by a one-stage clotting assay, whereas a similar specific activity was observed using a chromogenic assay. As described in this Example 14, the activity of factor VIII forms following saturation mutagenesis at residue 113 and the thrombin activation of the E113A form. Factor Xa generation assays performed on synthetic membrane and platelets are employed to determine kinetic and binding parameters for factor Xase comprised of the factor VIII E113A and wild type.

Factor VIII molecules bearing single point mutation of Glu113Ala were constructed from B domainless-factor VIII cDNA as described in Example 1 above, (using HSQ-MSAB-NotI-RENeo, obtained from Dr. Pete Lollar and John Healey). The factor VIII expression vector constructs were transfected in BHK cells and the mutant proteins were purified by SP-sepharose.

Saturation mutagenesis and the transient expression of factor VIII, substituting every amino acid except Asp for residue 113 was constructed and transiently expressed in COS-7 cells. Factor VIII activity in the conditioned medium (2 day) was measured by a one-stage clotting assay.

Factor VIII cofactor activity, factor IXa-factor VIIIa affinity, and kinetic parameters were determined using factor Xa generation assays. Reactions were performed in the presence of either phospholipid vesicles, non-activated platelets, or platelets activated by SFLLRN-amide (50 µM).

Figure 7:
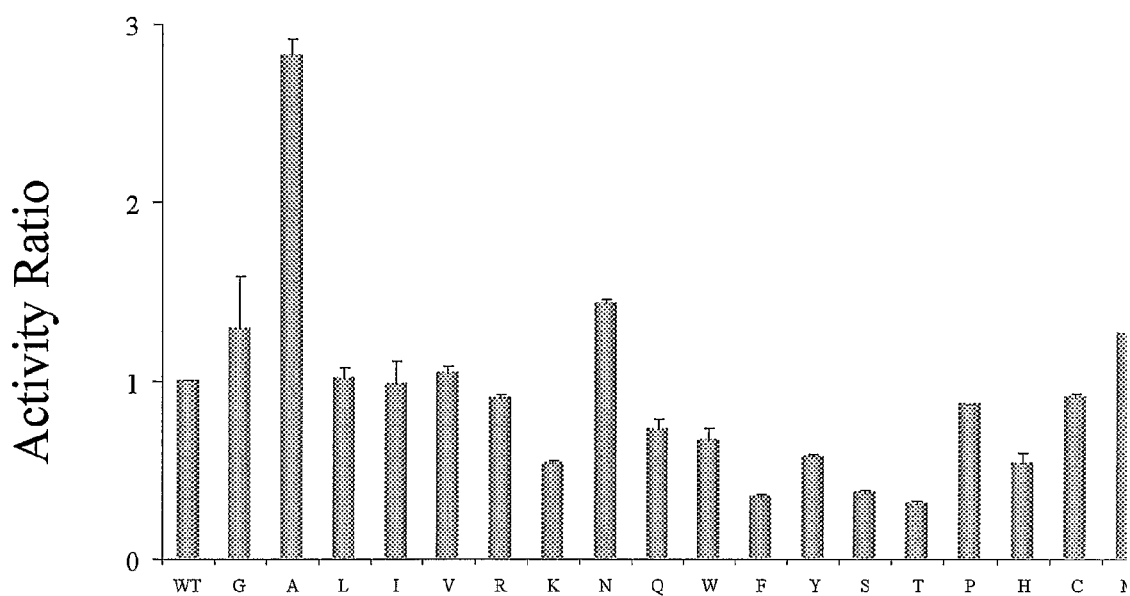
FIG. 7 is a graph showing clotting activity following saturation mutagenesis at E113. The single letter designation for amino acids corresponds to the substituted amino acid for each mutant. Activity is presented relative to a transfected wild type control normalized to a value=1.

As shown in FIG. 7, E113A possessed the greatest increase in activity relative to wild type (~3-fold). Substitution with Gly, Asn, or Met yielded modest activity increases (<50%), while Leu, Ile, Val, Pro, Cys, and Arg showed little if any effect. On the other hand, Lys, Gln, Trp, Tyr, Pro, His, Phe, Ser, and Thr were observed to be somewhat detrimental to activity with the latter three showing the greatest reductions in activity (at least 50%).

As shown in FIG. 8, factor VIII E113A and wild type (10 nM each) were activated by thrombin (5 nM) and activity was monitored by one-stage clotting assay. Activity is expressed as a ratio to the non-activated factor VIII activity at time 0. Both forms were activated ~40-fold, which occurred over a similar time course (FIG. 8). Furthermore, at all time points, E113A possessed about twice the activity as wild type. In addition, both activated forms decayed at similar rates suggesting that this mutation did not alter in the affinity of the A2 subunit within the factor VIIIa molecule.

As shown in Table 3 (below), both wild type and E113A bind to factor IXa with high affinity ($K_d$~5 nM) on phospholipid vesicles with <10% increase in $k_{cat}$. However, on the platelet surface, wild type binds factor IXa with lower affinity ($K_d$~20-25 nM) while E113A binding was unchanged ($K_d$~6 nM).

TABLE 3

Summary of Binding and Kinetic Parameters for Factor Xase Complexes

|  | Wild Type (WT) | E113 A |
|---|---|---|
| On Phospholipid Vesicles: | | |
| $K_d$ (nM) | 4.6 ± 0.3 | 5.0 ± 0.7 |
| $K_m$ (nM) | 23.8 ± 3.1 | 32.3 ± 2.2 |
| $K_{cat}$ (min$^{-1}$) | 225 ± 6 | 240 ± 15 |
| On Activated Platelets: | | |
| $K_d$ (nM) | 20.3 ± 5.1 | 6.0 ± 1.4 |
| Vmax (nMmin$^{-1}$) | 23.8 ± 2.9 | 18.9 ± 1.8 |
| $K_m$ (nM) | 14.3 ± 0.8 | 18.0 ± 1.1 |
| Vmax (nMmin$^{-1}$) | 10.4 ± 0.2 | 14.7 ± 0.3 |
| On Non-Activated Platelets: | | |
| $K_d$ (nM) | 25.6 ± 2.5 | 5.7 ± 0.6 |
| Vmax (nMmin$^{-1}$) | 3.1 ± 0.2 | 2.5 ± 0.1 |
| $K_m$ (nM) | 16.7 ± 7.2 | 41.9 ± 16.8 |
| Vmax (nMmin$^{-1}$) | 0.4 ± 0.1 | 1.2 ± 0.2 |

The activation of platelets resulted in increases in the Vmax values, while $K_m$ values were unchanged. The apparent increased Vmax for E113A compared with wild type in FIG. 10B reflects sub-saturating levels of the factor VIIIa forms.

A ~2-fold increase was observed in the activity of factor VIII E113A in a one-stage clotting assay. This increased activity was not likely a result of increased affinity for $Ca^{2+}$, since assays were performed at saturating $Ca^{2+}$ levels.

Saturation mutagenesis at position 113 (FIG. 7) revealed that substitution at this position with relatively small, nonpolar residues was well-tolerated, whereas replacement with a number of polar or charged residues was detrimental to activity. Thus residue 113 appears to contribute, directly or indirectly to factor VIII function. Ala-substitution yielded the greatest activity value.

Similar rates of activation and inactivation of E113A as observed for factor VIII wild type (FIG. 8) indicated that altered interactions with thrombin or the inter-subunit affinity factor VIIIa E113A do not contribute its increased activity.

Figure 9A:
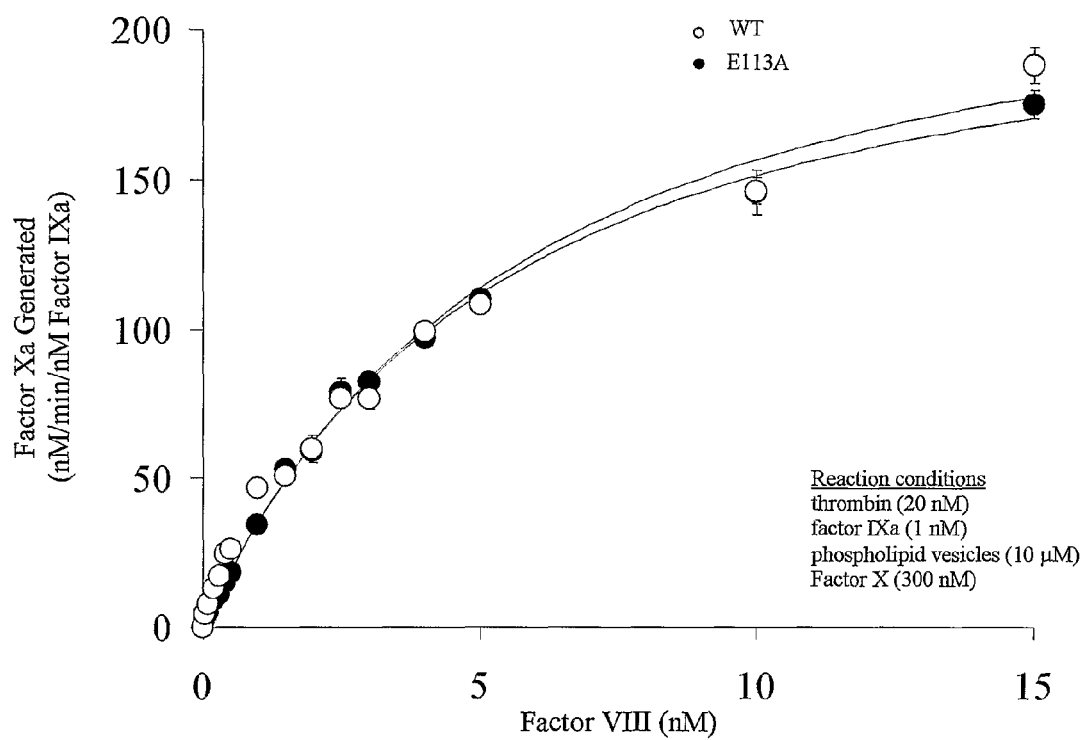
FIGS. 9A and 9B are graphs showing factor VIII activity determined by a factor Xa generation assay on phospholipids vesicles.
Figure 9B:
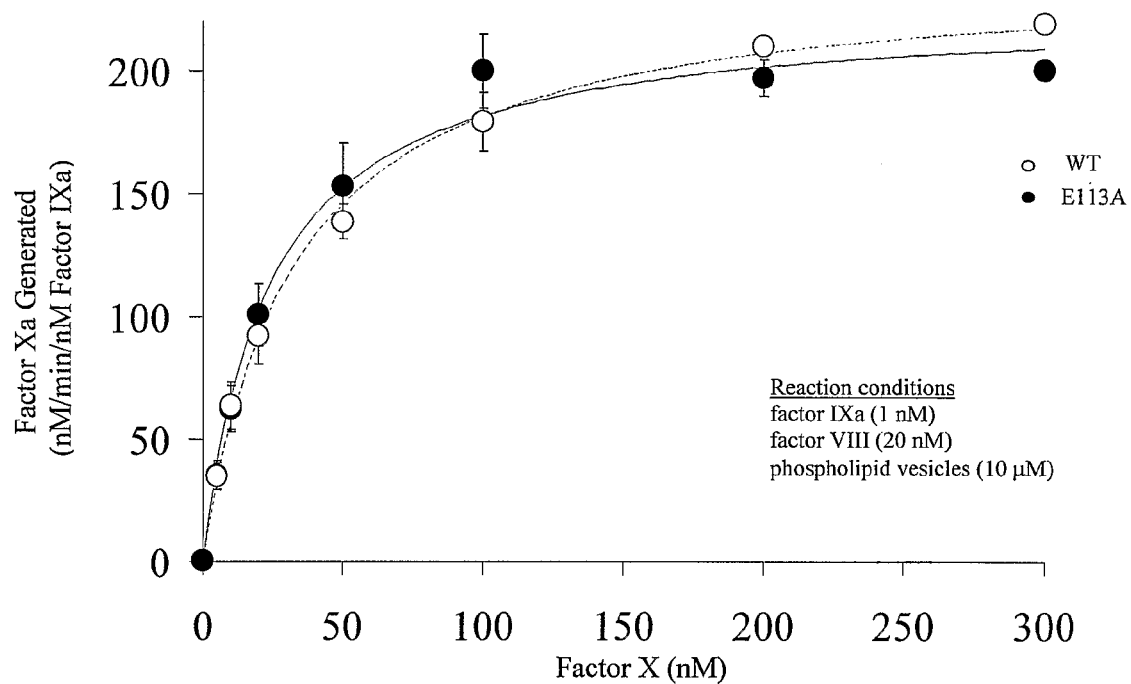
Figure 10A:
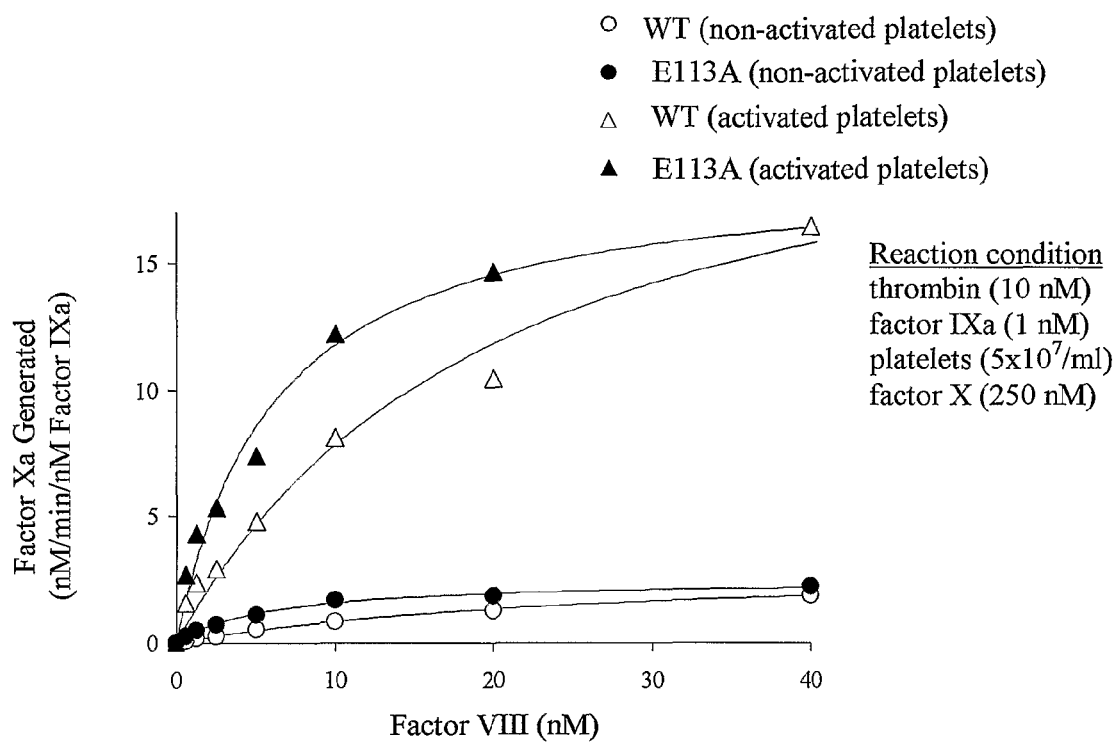
FIGS. 10A and 10B are graphs showing factor VIII activity determined by a factor Xa generation assay on platelets.
Figure 10B:
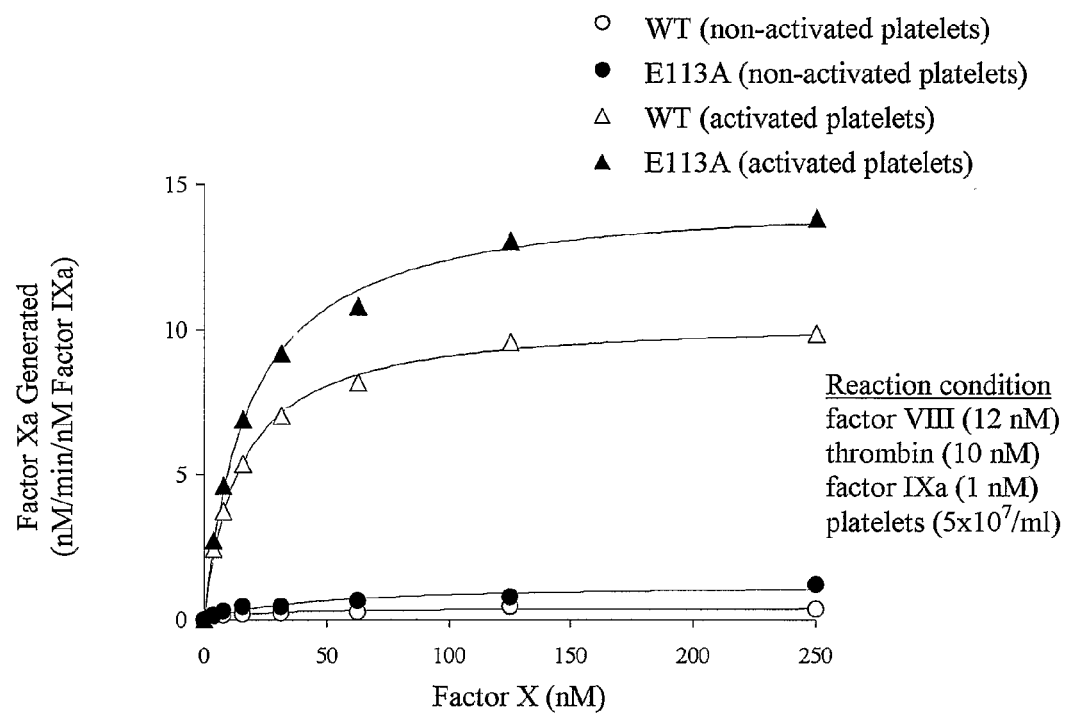

Results from factor Xa generation assays performed on synthetic phospholipid vesicles showed the mutant possessed similar values for specific activity, $K_m$ for substrate factor X, $k_{cat}$ for factor Xa generation and $K_d$ for factor IXa as compared with factor VIII wild type (FIGS. 9A-B). However, using platelet surfaces, significantly higher affinity was observed for the E113A-factor IXa interaction compared with that for WT (FIGS. 10A-B).

Since low levels (sub-nM) of factors VIIIa and IXa are generated during clotting in plasma, the enhanced affinity of factor VIII E113A for factor IXa may represent a novel factor VIII form for the treatment of hemophilia.

The factor VIII mutation E113A enhances the affinity for factor IXa on physiologic surfaces. This alteration may reflect the increased specific activity of E113A measured in a one-stage clotting assay where low levels of factor IXa may be generated.

Atomic surface modeling results show that the 110-126 region resides within A1 domain in close proximity to C1 domain but far removed from both surface and factor IXa interactive sites. Thus, indirect mechanisms appear to be involved in the surface-dependent modulation of factor IXa binding affinity due to the E113A mutation.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A recombinant factor VIII comprising an A1 domain having a calcium binding site according to one of SEQ ID NOS: 4-7 except for a substitution of the glutamic acid residue at the fourth residue of SEQ ID NOS: 4-7, wherein the recombinant factor VIII has a specific activity, as measured in a one-stage clotting assay, that is higher than that of a corresponding wild-type factor VIII.

2. The recombinant factor VIII according to claim 1, wherein the substitution is selected from the group consisting of alanine, valine, isoleucine, leucine, asparagine, glycine, and methionine.

3. The recombinant factor VIII according to claim 1, wherein the substitution is alanine.

4. The recombinant factor VIII according to claim 1, wherein the recombinant factor VIII has a specific activity at least about twice as great as the activity of the wild-type factor VIII.

5. The recombinant factor VIII according to claim 1, wherein the recombinant factor VIII is B domainless.

6. The recombinant factor VIII according to claim 1, wherein the recombinant factor VIII has a circulating half-life value that is equivalent to or greater than that of the wild-type factor VIII.

7. The recombinant factor VIII according to claim 1, wherein the recombinant factor VIII is substantially pure.

8. A pharmaceutical composition comprising the recombinant factor VIII according to claim 1.

9. The pharmaceutical composition according to claim 8 further comprising a stabilizer.

10. The pharmaceutical composition according to claim 8 further comprising a delivery vehicle.

11. The pharmaceutical composition according to claim 8 further comprising a pharmaceutically acceptable carrier.

12. A method of treating an animal for hemophilia A, the method comprising:
   administering to an animal exhibiting hemophilia A an effective amount of the recombinant factor VIII according to claim 1, whereby the animal exhibits effective blood clotting following vascular injury.

13. The method according to claim 12, wherein the effective amount comprises between about 10 to about 50 units/kg body weight of the animal.

14. The method according to claim 12 wherein the animal is a mammal.

15. The method according to claim 14 wherein the mammal is selected from the group consisting of human, rat, mouse, guinea pig, dog, cat, monkey, chimpanzee, orangutan, cow, horse, sheep, pig, goat, rabbit, and chicken.

16. The method according to claim 12 further comprising: periodically repeating said administering.

* * * * *

UNITED STATES PATENT AND TRADEMARK OFFICE
CERTIFICATE OF CORRECTION

| | | |
|---|---|---|
| PATENT NO. | : 7,855,274 B2 | Page 1 of 1 |
| APPLICATION NO. | : 10/581471 | |
| DATED | : December 21, 2010 | |
| INVENTOR(S) | : Fay et al. | |

It is certified that error appears in the above-identified patent and that said Letters Patent is hereby corrected as shown below:

Column 1, line 11, insert --, HL 76213,-- after "HL 38199"; and
line 12, delete "may retain" and insert --has-- in its place.

Signed and Sealed this
Twenty-ninth Day of March, 2011

David J. Kappos
*Director of the United States Patent and Trademark Office*